United States Patent
Hosomi

(10) Patent No.: US 9,284,603 B2
(45) Date of Patent: Mar. 15, 2016

(54) TARGET SEQUENCE AMPLIFICATION METHOD, POLYMORPHISM DETECTION METHOD, AND REAGENTS FOR USE IN THE METHODS

(75) Inventor: Toshiya Hosomi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 779 days.

(21) Appl. No.: 13/388,272

(22) PCT Filed: Jan. 21, 2011

(86) PCT No.: PCT/JP2011/051061
§ 371 (c)(1),
(2), (4) Date: Jan. 31, 2012

(87) PCT Pub. No.: WO2011/090154
PCT Pub. Date: Jul. 28, 2011

(65) Prior Publication Data
US 2012/0129174 A1    May 24, 2012

(30) Foreign Application Priority Data
Jan. 21, 2010    (JP) .................................. 2010-011470

(51) Int. Cl.
*C12P 19/34*    (2006.01)
*C12Q 1/68*    (2006.01)

(52) U.S. Cl.
CPC .................................... *C12Q 1/6858* (2013.01)

(58) Field of Classification Search
CPC ........... C12Q 1/6858; C12Q 2535/125; C12Q 2525/161; C12Q 2527/107
USPC ................................................. 435/91.2, 6.1
See application file for complete search history.

(56) References Cited

U.S. PATENT DOCUMENTS

| | | | |
|---|---|---|---|
| 4,889,818 A | 12/1989 | Gelfand et al. | 435/194 |
| 5,079,352 A | 1/1992 | Gelfand et al. | 536/27 |
| 5,972,602 A | 10/1999 | Hyland et al. | |
| 6,472,156 B1 | 10/2002 | Wittwer et al. | |
| 2003/0224434 A1 | 12/2003 | Wittwer et al. | |
| 2007/0154892 A1 | 7/2007 | Wain-Hobson et al. | |
| 2007/0184457 A1 | 8/2007 | Pont-Kingdon et al. | |
| 2008/0044812 A1 | 2/2008 | Molloy et al. | |
| 2009/0104616 A1 | 4/2009 | Hosomi | 435/6 |
| 2009/0208954 A1 | 8/2009 | Hirai et al. | 435/6 |
| 2009/0208956 A1 | 8/2009 | Hirai et al. | 435/6 |
| 2009/0269756 A1 | 10/2009 | Majima et al. | 435/6 |
| 2010/0112559 A1 | 5/2010 | Hirai et al. | 435/6 |
| 2010/0297617 A1 | 11/2010 | Hirai et al. | 435/6 |
| 2011/0117568 A1 | 5/2011 | Hirai et al. | |

FOREIGN PATENT DOCUMENTS

| | | | | |
|---|---|---|---|---|
| EP | 0 332 435 | 9/1989 | ............... | C12Q 1/68 |
| EP | 0 455 430 | 11/1991 | | |
| EP | 1619258 A1 | 1/2006 | | |
| EP | 1686190 | * | 8/2006 | |
| EP | 1686190 A1 | 8/2006 | | |
| EP | 1 686 190 | 4/2008 | ............... | C12Q 1/68 |
| EP | 2025764 | * | 2/2009 | |
| EP | 2314680 A1 | 4/2011 | | |
| JP | 2853864 | 2/1990 | ............... | C12Q 1/68 |
| JP | 2004-337124 | 12/2004 | ............... | C12N 15/09 |
| JP | 2006-230401 | 9/2006 | ............... | C12Q 1/68 |
| WO | WO 91/09950 | 7/1991 | ............... | C12N 15/54 |
| WO | WO 92/09689 | 6/1992 | ............... | C12N 15/00 |
| WO | WO 2006/133184 | 12/2006 | | |
| WO | WO 2008/066136 | 6/2008 | ............... | C12N 15/00 |
| WO | WO 2008/066161 | 6/2008 | ............... | C12N 15/00 |
| WO | WO 2008/066162 | 6/2008 | ............... | C12Q 1/68 |
| WO | WO 2008/066163 | 6/2008 | ............... | C12N 15/09 |
| WO | WO 2008/066164 | 6/2008 | ............... | C12N 15/09 |

(Continued)

OTHER PUBLICATIONS

International Search Report for PCT/JP2011/051061 (mailed Apr. 19, 2011).

Crockett et al., "Fluorescein-Labeled Oligonucleotides for Real-Time PCR: Using the Inherent Quenching of Deoxyguanosine Nucleotides", Analytical Biochemistry, 290:89-97 (2001).

Germer et al., "Single-Tube Genotyping without Oligonucleotide Probes", Genome Res., 9(1):72-79 (1999).

Office Action issued in related European Patent Application No. 09773547.6 dated Nov. 7, 2013.

(Continued)

*Primary Examiner* — Cynthia B Wilder
(74) *Attorney, Agent, or Firm* — Morgan, Lewis & Bockius LLP

(57) ABSTRACT

An object of the present invention is to provide an amplification method that inhibits amplification caused by erroneous annealing of a primer. Primers X1 and X2 are used in amplification of a target sequence including a target site showing a polymorphism. The primer X1 includes a sequence A1' and a sequence E1. The sequence A1' is complementary to a partial sequence A1 in a template nucleic acid, and has, in its 3' region, a base x1' complementary to a first base x1 at the target site in a 5' region of the sequence A1. The sequence E1 is noncomplementary to a partial sequence B1 adjacent to the 3' end of the partial sequence A1 in the template nucleic acid, and is bound to the 5' end of the partial sequence A1'. The primer X2 includes a sequence A2'. The sequence A2' is complementary to a partial sequence A2 in the template nucleic acid, and has, in its 3' region, a base x2' complementary to a second base x2 at the target site in a 5' region of the partial sequence A2. Each of the primers X1 and X2 has a base complementary to the target site in its 3' region. By these primers, when only a template in which the target site is the first base x1 is present, erroneous amplification of the target sequence having the second base x2 can be prevented. Thus, a false positive for the polymorphism of the second base x2 can be inhibited.

10 Claims, 6 Drawing Sheets

(56) References Cited

FOREIGN PATENT DOCUMENTS

| WO | WO 2008/066165 | 6/2008 | ............ C12N 15/00 |
|----|----------------|--------|---------|
| WO | 2010/001969 A1 | 1/2010 | |

OTHER PUBLICATIONS

Extended European Search Report issued in corresponding European Patent Application No. 11734760.9 dated Jan. 8, 2014.
Wang et al., "High-throughput SNP genotyping by single-tube PCR with Tm-shift primers," BioTechniques, 39: 885-893 (2005).
Office Action issued in technically related Chinese Patent Application No. 200980125546.7 dated Feb. 29, 2012.
Zhou, Chenhui et al., "Application of a Bidirectional Amplification of Specific Alleles Polymerase Chain Reaction Technique in Study of SNPs." Journal of Chongquing Medical University, 31: 658-661 (2006), English abstract only.
Extended European Search Report issued in a related European Application No. 09773547.6, dated Nov. 14, 2011.
Casado-Diaz et al., "Individual single tube genotyping and DNA pooling by allele-specific PCR to uncover associations of polymorphisms with complex diseases," Clinica Chimica Acta, 376: 155-162 (2007).
Rust et al., "Mutagenically separated PCR (MS-peR): a highly specific one step procedure for easy mutation detection," Nucleic Acids Research, 21(16): 3623-3629 (1993).
Senescau et al., "Use of a locked-nucleic-acid oligomer in the clamped-probe assay for detection of a minority *Pfcrl* K67T mutant population of *Plasmodium falciparum*," Journal of Clinical Microbiology, 43(7): 3304-3308 (2005).
Office Action issued in related U.S. Appl. No. 13/002,194 dated Aug. 26, 2014.
Office Action issued in corresponding European Patent Application No. 11734760.9 dated Jul. 27, 2015.

* cited by examiner

○ : Normal base
● : Mutant base
▭ : Additional sequence (E1)

○ : Normal base
● : Mutant base
▭ : Additional sequence (E1)
▬ : Additional sequence (E2)

```
                              SEQUENCE LISTING

<160> NUMBER OF SEQ ID NOS: 7

<210> SEQ ID NO 1
<211> LENGTH: 599
<212> TYPE: DNA
<213> ORGANISM: Homo sapiens

<400> SEQUENCE: 1
cagcctctcc ctgcgtaaat tcaagttcac tggcttgaga agaagaaaag agcctggcca        60
tgtccctccc acacgagcac agtctcagga tgcaggtgct tgggaccatg ttggaagttg       120
ggcccaggac tgaggagcag agtcagaatc cttcagaagg cttttttcttt agacagttgt      180 ttgttcagtt gggagcggag ccacgtgttg aagtctcgtt gtcttgttgg cagggtctg        240 cacccgggag cccccgttct atatcatcay tgagttcatg acctacggga acctcctgga      300
ctacctgagg gagtgcaacc ggcaggaggt gaacgccgtg gtgctgctgt acatggccac      360
tcagatctcg tcagccatgg agtacctgga gaagaaaaac ttcatccaca ggtaggggcc     420
tggccaggca gcctgcgcca tggagtcaca gggcgtggag ccgggcagcc ttttacaaaa     480
agccccagcc taggaggtct cagggcgcag cttctaacct cagtgctggc aacacattgg    540
accttggaac aaaggcaaac actaggctcc tggcaaagcc agctttgggc atgcatcca     599

<210> SEQ ID NO 2
<211> LENGTH: 33
<212> TYPE: DNA
<213> ORGANISM: Artificial
<220> FEATURE:
<223> OTHER INFORMATION: primer

<400> SEQUENCE: 2
ggacggacgg accgtcctcg ttgtcttgtt ggc                                    33

<210> SEQ ID NO 3
<211> LENGTH: 27
<212> TYPE: DNA
<213> ORGANISM: Artificial
<220> FEATURE:
<223> OTHER INFORMATION: primer

<400> SEQUENCE: 3
ctacgttccc gtaggtcatg aactcag                                           27

<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4
ttcccgtagg tcatgaactc ag                                                22

<210> SEQ ID NO 5
<211> LENGTH: 25
<212> TYPE: DNA
<213> ORGANISM: Artificial
<220> FEATURE:
<223> OTHER INFORMATION: primer

<400> SEQUENCE: 5
```

```
aggttcccgt aggtcatgaa ctcaa                                    25

<210> SEQ ID NO 6
<211> LENGTH: 20
<212> TYPE: DNA
<213> ORGANISM: Artificial
<220> FEATURE:
<223> OTHER INFORMATION: probe

<400> SEQUENCE: 6
ctcaatgatg atatagaacg                                          20

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
tgctcaggtt cccgtaggtc atgaactcaa                               30
```

TARGET SEQUENCE AMPLIFICATION METHOD, POLYMORPHISM DETECTION METHOD, AND REAGENTS FOR USE IN THE METHODS

CROSS-REFERENCE TO RELATED APPLICATIONS

This application is the U.S. National Phase under 35 U.S.C. §371 of International Application PCT/JP2011/051061, filed Jan. 21, 2011, which claims priority to JP Application No. 2010-011470, filed Jan. 21, 2010, which are hereby incorporated by reference in their entirety.

SEQUENCE LISTING SUBMISSION VIA EFS-WEB

A computer readable text file, entitled "068022-5119-SequenceListing.txt," created on or about Jan. 31, 2012 with a file size of about 3 kb contains the sequence listing for this application and is hereby incorporated by reference in its entirety.

TECHNICAL FIELD

The present invention relates to a method for amplifying a target sequence that includes a target site showing a target polymorphism, a method for detecting a polymorphism, and reagents for use in these methods.

BACKGROUND ART

In prevention and treatment of diseases, detection of gene mutations including single nucleotide polymorphisms (SNPs) has been carried out widely. For example, the gene of a cancer cell has many mutations, and it is known that these mutations are involved in canceration of the cell. Thus, by detecting the gene mutations in the cell, it is possible to check the possibility of canceration, the stage of cancer progression, and the like, which are considered to be very useful information in treatment. Also, a gene mutation that causes a cancer cell to exhibit a drug resistance has been reported. By detecting this mutation, the effectiveness of a drug to a patient can be determined, which enables more appropriate treatment. For example, regarding chronic myelocytic leukemia (CML) to which medication with an anticancer drug "imatinib" is applied widely, a mutation in the bcr-abl gene (e.g., T315I) is considered to affect the drug resistance. As described above, the detection of gene mutations is useful for early detection and treatment of diseases in the field of clinical practice, so that high reliability of the detection is demanded.

As methods for detecting gene mutations, an ASP (Allele Specific Primer)-PCR (Polymerase Chain Reaction) method (Japanese Patent No. 28538641 and a Tm (Melting temperature) analysis method (Crockett et al., Analytical Biochemistry, 290(1):89-97 (2001)) are known generally. The ASP-PCR method is a method in which PCR is performed using a primer that is complementary to a sequence including a target site and has, in its 3' region, a base complementary to the base at the target site, thereby amplifying the target sequence including the target site to determine a mutation. For example, in the case where a mutant primer designed so that the target site is a mutant base is used as the primer, the gene examined can be determined as "mutant" if amplification is observed and as "normal" if no amplification is observed. On the other hand, in the case where a normal primer designed so that the target site is a normal base is used as the primer, the gene examined can be determined as "normal" if amplification is observed and as "mutant" if no amplification is observed. In the Tm analysis, for example, first, a target sequence including a target site in a gene is amplified, and thereafter, a hybrid (double-stranded nucleic acid) of the thus-obtained amplification product with a probe that can hybridize to the sequence including the target site is formed. This hybrid is then heat-treated, and dissociation (melting) of the hybrid into single-stranded nucleic acids accompanying the temperature rise is detected by measuring signals such as absorbances, thereby determining the Tm value. Then, based on this Tm value, the mutation is determined. The Tm value becomes higher as the complementarity between the single-stranded nucleic acids composing the hybrid becomes higher, and becomes lower as the complementarity between the same becomes lower. Thus, for example, by using a mutant probe designed so that the target site is a mutant base (X) as the above-described probe, the mutation can be determined in the following manner. First, the Tm value of a hybrid of a target sequence in which the target site is a mutant base with the mutant probe is determined previously (an evaluation standard Tm value). On the other hand, as described above, the Tm value of a hybrid of an amplification product obtained by amplifying the gene with the mutant probe is determined (a measured Tm value). Then, the evaluation standard Tm value and the measured Tm value are compared with each other. As a result, if the measured Tm value is the same as the evaluation standard Tm value, it can be determined that the target sequence of the amplification product shows a perfect match with the probe, i.e., the target site is the mutant base (X), and the mutation is present. On the other hand, if the measured Tm value is lower that the evaluation standard Tm value, the target sequence of the amplification product shows a mismatch with the probe, so that it can be determined that the target site is a normal base (Y), and no mutation is present.

However, the ASP-PCR method has a problem in that it lacks the specificity although it is excellent in sensitivity. For example, when the mutant primer is used, even if no mutation is present at the target site, amplification may be observed, resulting in a false positive. Furthermore, in the ASP-PCR method, only either one of the mutant primer and the normal primer can be used in a single reaction system. Thus, in order to check whether the target site is mutant or normal, it is necessary to perform PCR in two kinds of reaction systems, namely, a reaction system in which the mutant primer is used and a reaction system in which the normal primer is used. Since the two kinds of reaction systems are used as described above, the process thereof is complex and it requires time and costs. On the other hand, the Tm analysis is excellent in specificity, so that the problem of false positives can be avoided. Besides, whether the target site is normal or mutant can be determined in a single reaction system. However, the Tm analysis method has a problem in that it cannot achieve a sufficient sensitivity.

In particular, as described above, when a gene mutation in cancer cells is to be detected, cells having mutant target genes and cells having normal target genes are preset together in a specimen collected from a patient. Thus, for example, it is required to detect the presence or absence of mutation accurately even in a biological sample containing a large amount of normal genes and a small amount of mutant genes.

BRIEF SUMMARY OF THE INVENTION

Problem to be Solved by the Invention

Under such circumstances, the inventors of the present invention have established a novel polymorphism detection method that uses a normal primer and a mutant primer and further uses a probe. The normal primer is a primer for amplifying a normal target sequence in which a target site is a normal base. The mutant primer is a primer for amplifying a mutant target sequence in which a target site is a mutant base. The probe is a probe that can hybridize to a sequence including the target site. Specifically, in a single reaction system containing the normal primer and the mutant primer, a template nucleic acid is subjected to an amplification reaction, and further, Tm analysis is conducted using the probe to detect a polymorphism. According to this method, since both the normal primer and the mutant primer are used, both the normal target sequence and the mutant target sequence can be amplified specifically. Then, the Tm analysis using the probe is conducted, so that a normal gene and a mutant gene can be detected in a single reaction system. Furthermore, for example, when only a normal template nucleic acid is present, the normal primer anneals to the normal template nucleic acid more preferentially than the mutant primer, so that erroneous amplification due to the annealing of the mutant primer is inhibited. Thus, in the polymorphism detection using the probe, a false positive for the mutant gene can be prevented. As described above, according to this method, it is possible to determine whether the target site is normal or mutant, or whether there are both the normal and mutant target sites with high reliability in a single reaction system.

However, as a result of further study, it was found that, depending on conditions, there is a risk that false positives may occur in the Tm analysis after the amplification reaction. Specifically, there is such a risk in the following cases, for example: when a biological sample such as blood is subjected to amplification without being purified; when polymerase is present in an amount larger than usual in an amplification reaction; and when an annealing temperature of a primer is lower than usual. Under such conditions, the mutant primer may anneal to the normal target sequence, whereby a mutant target sequence is amplified, resulting in a false positive for a mutant gene.

With the foregoing in mind, it is an object of the present invention to provide, for example: an amplification method that can inhibit amplification resulting from erroneous annealing of a primer, regardless of the nucleic acid sample to be used and the conditions of the amplification reaction; a polymorphism detection method in which the occurrence of a false positive can be inhibited by the amplification method; and reagents for use in these methods.

Means for Solving Problem

In order to achieve the above object, the present invention provides a method for amplifying a target sequence, including the step of: amplifying a target sequence in a template nucleic acid in a reaction system containing primers (X1) and (X2) shown below. The target sequence includes a target site showing a polymorphism, and a base (x) at the target site is either a first base (x1) or a second base (x2).
Primer (X1):
The primer (X1) includes a sequence (A1') and a sequence (E1). The sequence (A1') is complementary to a partial sequence (A1) in the template nucleic acid, and has, in its 3' region, a base (x1') complementary to the first base (x1) at the target site in the 5' region of the partial sequence (A1). The sequence (E1) is noncomplementary to a partial sequence (B1) adjacent to the 3' end of the partial sequence (A1) in the template nucleic acid, and is bound to the 5' end of the sequence (A1').

Primer (X2):
The primer (X2) includes a sequence (A2'). The sequence (A2') is complementary to a partial sequence (A2) in the template nucleic acid, and has, in its 3' region, a base (x2') complementary to the second base (x2) at the target site in the 5' region of the partial sequence (A2).

The present invention also provides a method for detecting a polymorphism, including the steps of: amplifying a target sequence including a target site in a template nucleic acid by the amplification method according to the present invention; and detecting a polymorphism at the target site in the target sequence with a probe that can hybridize to the target sequence.

The present invention also provides an amplification reagent for use in the amplification method according to the present invention. A target sequence in a template nucleic acid includes a target site showing a polymorphism. A base (x) at the target site is either a first base (x1) or a second base (x2). The amplification reagent contains the above-described primers (X1) and (X2).

The present invention also provides a detection reagent for use in the polymorphism detection method according to the present invention. The detection reagent contains: the amplification reagent according to the present invention; and a probe that can hybridize to the target sequence including the target site in the template nucleic acid.

Effects of the Invention

According to the present invention, it is possible to prevent erroneous annealing of a primer, for example. As a result, a false positive is inhibited, thereby allowing polymorphism detection to be performed with high reliability. Therefore, it can be said that the present invention is very useful in the field of recent clinical practice where treatment and diagnosis are carried out based on the detection of gene polymorphism, for example.

MODE FOR CARRYING OUT THE INVENTION

The inventors of the present invention conducted diligent study, and as a result, they obtained new findings about the cause of false positives. This will be described below with reference to FIG. 4. FIG. 4 shows schematic views showing annealing of a normal primer and a mutant primer, as well as extended strands generated from these primers. In a normal template nucleic acid, a target site is a normal base. The sequence of the normal primer is complementary to a partial sequence including the normal base in the normal template nucleic acid. In a mutant template nucleic acid, a target site is a mutant base. The sequence of the mutant primer is complementary to a partial sequence including the mutant base in the mutant template nucleic acid. In FIG. 4, strands to which the normal primer and the mutant primer can anneal are defined as "forward strands", which are indicated with "(+)". The normal primer, the mutant primer, and strands extended therefrom are defined as "reverse strands". In FIG. 4, the normal primer and the mutant primer are reverse primers for extending the reverse strands. In FIG. 4, an open circle indicates a normal base, and a filled circle indicates a mutant base (the same applies hereinafter).

Figure 4A:
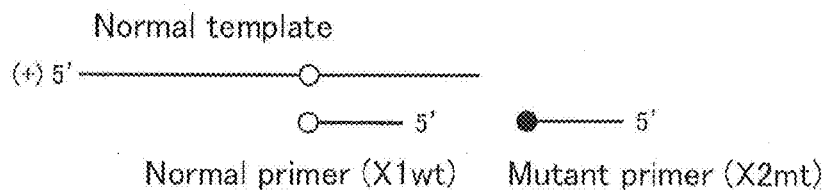
FIG. 4 shows schematic views showing still another example of annealing of the primers and extended strands resulting therefrom.
Figure 4B:
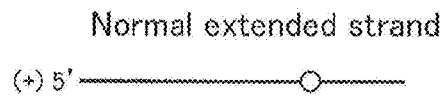
Figure 4C:
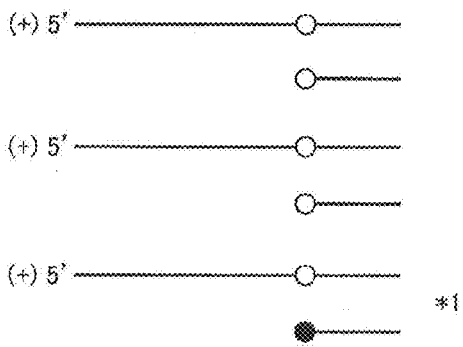
Figure 4D:
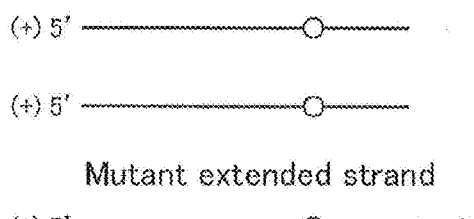
Figure 4E:
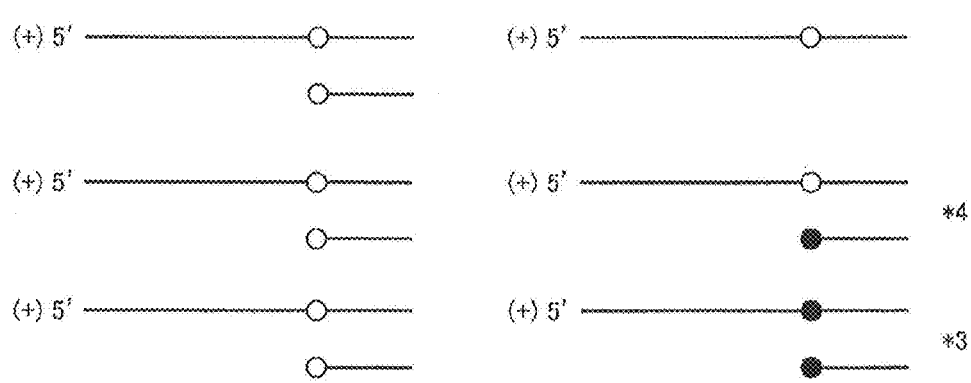

When the normal primer and the mutant primer are used as reverse primers, there is a possibility that false positives may occur for the following reasons, for example. When only the normal template nucleic acid (+) is present as a template nucleic acid, the normal primer generally is more likely to anneal to the normal template nucleic acid (+) than the mutant primer (FIG. 4A). Thus, from the normal primer, a normal extended strand (−) is generated as a reverse strand, and further, from a forward primer, a normal extended strand (+) is generated as a forward strand (FIG. 4B). However, the mismatch between the mutant primer and the normal extended strand (+) is only one base at the target site. Thus, as shown in FIG. 4C, not only the normal primer but also the mutant primer may anneal to the normal extended strand (+), although the annealing of the mutant primer occurs at a very low probability (*1 in FIG. 4C). As a result of such annealing of the mutant primer, as shown in FIG. 4D, even if no mutant template nucleic acid is present, a mutant extended strand (+) in which the target site has been substituted with a mutant base is generated in addition to the normal extended strand (+) (*2 in FIG. 4D). Then, as shown in FIG. 4E, since the mutant primer is more likely to anneal to the mutant extended strand (+) than the normal primer, amplification of the mutant extended strand (+) occurs repeatedly (*3 in FIG. 4E). Moreover, the above-described erroneous annealing of the mutant primer to the normal extended strand (+) may occur in any cycle of the amplification reaction. Thus, annealing of the mutant primer to the normal extended strand (+) newly occurs (*4 in FIG. 4E). As described above, owing to the annealing of the mutant primer to the normal extended strand, mutant extended strands may be generated. Thus, as a result, there is a possibility that mutant extended strands may be generated in an amount sufficient for indication of a false positive in Tm analysis to be conducted subsequently.

With the foregoing in mind, the inventors of the present invention tried to find the way to prevent erroneous annealing of a primer as a cause of a false positive, and achieved the present invention.

In the present invention, in a template nucleic acid, a site at which a target polymorphism occurs is referred to as a "target site", and a sequence including the target site is referred to as a "target sequence". Hereinafter, when the target site is a mutant base ($x_{mt}$), the template nucleic acid is referred to as a "mutant template", the target sequence is referred to as a "mutant target sequence", and the gene is referred to as a "mutant gene". When the target site is a normal base ($x_{wt}$), the template nucleic acid is referred to as a "normal template", the target sequence is referred to as a "normal target sequence", and the gene is referred to as a "normal gene". The term "normal" also can be referred to as "wild-type", for example.

In the present invention, a nucleic acid contained in a reaction system before starting an amplification reaction is referred to as a "template nucleic acid", and a nucleic acid generated by the amplification reaction in the reaction system containing the template nucleic acid after the start of the amplification is referred to as an "amplification product or extended strand".

In the present invention, the template nucleic acid may be a single-stranded nucleic acid or a double-stranded nucleic acid. When the template nucleic acid is a double-stranded nucleic acid, it is only necessary that one of the two single strands composing the template nucleic acid is a strand to which the primers (X1) and (X2) can anneal. In the present invention, for the sake of convenience of explanation, a strand to which the primers (X1) and (X2) can anneal is referred to as a "forward strand or (+) strand" and the direction thereof is referred to as a "forward direction", and a strand complementary to the forward strand is referred to as a "reverse strand or (−) strand" and the direction thereof is referred to as a "reverse direction". Furthermore, a primer that anneals to the forward strand to extend the reverse strand, e.g., the primer (X1), the primer (X2), or the like, is referred to as a "reverse primer", and a primer that anneals to the reverse strand to extend the forward strand, e.g., a primer (Y1) or the like to be described below, is referred to as a "forward primer". It is to be noted, however, that these terms are used merely for the sake of convenience, and a strand to which the primers (X1) and (X2) can anneal may be a "reverse strand", for example. Furthermore, in the present invention, for the sake of convenience, the terms "forward strand (+)" and "the reverse strand (−)" are used for explanation. However, for example, when referring to a gene, either of the forward strand (+) and the reverse strand (−) can mean a sense strand or an antisense strand.

In the present invention, ends of a base sequence are the 5' end and the 3' end, which respectively mean endmost bases on the 5' side and the 3' side in the base sequence. Furthermore, a 5' region is a region including several bases from the 5' end of the base sequence, and a 3' region is a region including several bases from the 3' end of the base sequence. The several bases are not particularly limited, and mean 1 to 10, 1 to 4, 1 to 3, or 1 to 2 bases from the end, for example. In the present invention, the Zth base (Z is a positive integer) from an end of a base sequence is a numerical order counted with the base at the end as the first base. For example, the first base from the end means the base at the end, and the second base from the end means a base next to the base at the end.

<Amplification Method>

As described above, the method for amplifying a target sequence according to the present invention includes the step of: amplifying a target sequence in a template nucleic acid in a reaction system containing the primers (X1) and (X2). In this amplification method, the target sequence includes a target site showing a polymorphism, and a base (x) at the target site is either a first base (x1) or a second base (x2).

The primer (X1) includes a sequence (A1') and a sequence (E1). The sequence (A1') is complementary to a partial sequence (A1) in the template nucleic acid, and has, in its 3' region, a base (x1') complementary to the first base (x1) at the target site in a 5' region of the partial sequence (A1). The sequence (E1) is noncomplementary to a partial sequence (B1) adjacent to the 3' end of the partial sequence (A1) in the template nucleic acid, and is bound to the 5' end of the sequence (A1'). The sequence (E1) also is referred to as an additional sequence, for example. The primer (X2) includes a sequence (A2'). The sequence (A2') is complementary to a partial sequence (A2) in the template nucleic acid, and has, in its 3' region, a base (x2') complementary to the second base (x2) at the target site in a 5' region of the partial sequence (A2). In the setting of the primers (X1) and (X2), the above-described target site means the same site showing a polymorphism in the template nucleic acid.

The base (x) at the target site in the template nucleic acid is not particularly limited as long as it is a polymorphic base at the target site. For example, the base (x) may be a normal base ($x_{wt}$) or a mutant base ($x_{mt}$). Hereinafter, a primer designed so that the base at the target site (x) is a normal base ($x_{wt}$) is referred to as a "normal primer", and a primer designed so that the base at the target site (x) is a mutant base ($x_{mt}$) is referred to as a "mutant primer". When the first base (x1) is a normal base ($x_{wt}$) and the second base (x2) is a mutant base ($x_{mt}$), the primer (X1) is referred to as a normal primer ($X1_{wt}$), and the primer (X2) is referred to as a mutant primer ($X2_{mt}$). When the first base (x1) is a mutant base ($x_{mt}$) and the second base (x2) is a normal base ($x_{wt}$), the primer (X1) is referred to as a mutant primer ($X1_{mt}$), and the primer (X2) is referred to as a normal primer ($X2_{wt}$).

The reason why the above-described erroneous annealing of a primer can be prevented by the present invention will be described below with reference to FIGS. 1 and 2. The description will be made with reference to an illustrative example of the present invention where the first base (x1) is a normal base ($x_{wt}$), the primer (X1) is a normal primer ($X1_{wt}$), the second base (x2) is a mutant base ($x_{mt}$), and the primer (X2) is a mutant primer ($X2_{mt}$). These conditions and also the configurations shown in the drawings merely are illustrative, and the present invention is not limited thereto. Also, the present invention is not limited by the reason described below.

Figure 1A:
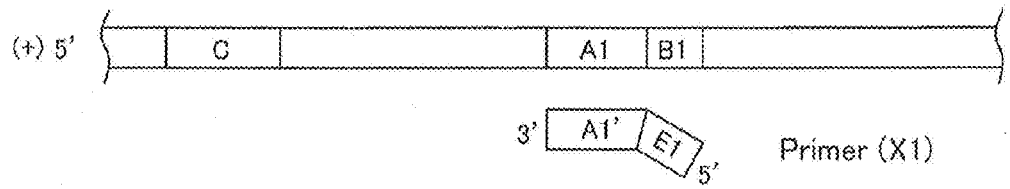
FIG. 1 shows schematic views showing an example of the primers of the present invention.
Figure 1B:
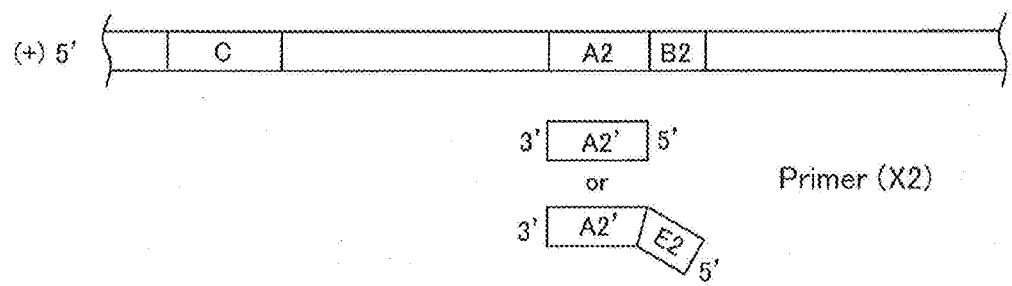

FIG. 1A is a schematic view showing the relationship between a normal template (e.g., a normal gene) and the normal primer ($X1_{wt}$). FIG. 1B is a schematic view showing the relationship between a mutant template (e.g., a mutant gene) and the mutant primer ($X2_{mt}$). In the normal template, the base (x) at the target site is a normal base ($x_{wt}$). In the mutant template, the base (x) at the target site is a mutant base ($x_{mt}$). FIG. 2 shows schematic views showing annealing of the normal primer ($X1_{wt}$) and the mutant primer ($X2_{mt}$), as well as extended strands generated from these primers. In FIGS. 1 and 2, strands to which the normal primer ($X1_{wt}$) and the mutant primer ($X2_{mt}$) can anneal are defined as forward strands, which are indicated with "(+)". The normal primer ($X1_{wt}$), the mutant primer ($X2_{mt}$), and extended strands generated from these primers are defined as reverse strands (the same applies hereinafter). In FIG. 2, an open circle indicates a normal base, and a filled circle indicates a mutant base (the same applies hereinafter).

First, the configuration of the normal primer ($X1_{wt}$) will be described. As shown in FIG. 1A, in the sequence of the normal template (+), a sequence including the normal base ($x_{wt}$) at the target site in its 5' region is previously determined as a partial sequence (A1), and a sequence adjacent to the 3' end of the partial sequence (A1) is previously determined as a partial sequence (B1). On the other hand, the normal primer ($X1_{wt}$) is configured so that it includes a sequence (A1') complementary to the partial sequence (A1) and a sequence (E1) noncomplementary to the partial sequence (B1). The partial sequence (E1) is bound to the 5' end of the sequence (A1'). In the normal primer ($X1_{wt}$), a complementary base ($x_{wt}'$) to be paired with the normal base ($x_{wt}$) is located in a 3' region of the sequence (A1').

Next, the configuration of the mutant primer ($X2_{mt}$) will be described. As shown in FIG. 1B, in the sequence of the mutant template (+), a sequence including a mutant base ($x_{mt}$) at the target site in its 5' region is previously determined as a partial sequence (A2). On the other hand, the mutant primer ($X2_{mt}$) is configured so that it includes a sequence (A2') complementary to the partial sequence (A2). In the mutant primer ($X2_{mt}$), a complementary base ($x_{mt}'$) to be paired with the mutant base ($x_{mt}$) is located in a 3' region of the sequence (A2'). Other configurations shown in FIG. 1 will be described below.

Figure 2A:
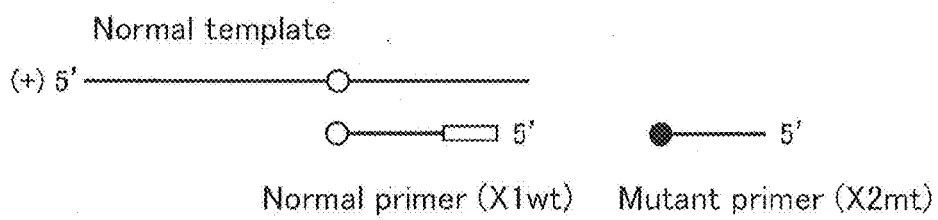
FIG. 2 shows schematic views showing an example of annealing of the primers of the present invention and extended strands resulting therefrom.
Figure 2B:
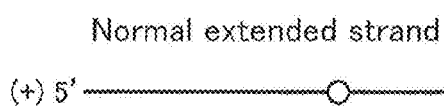
Figure 2C:
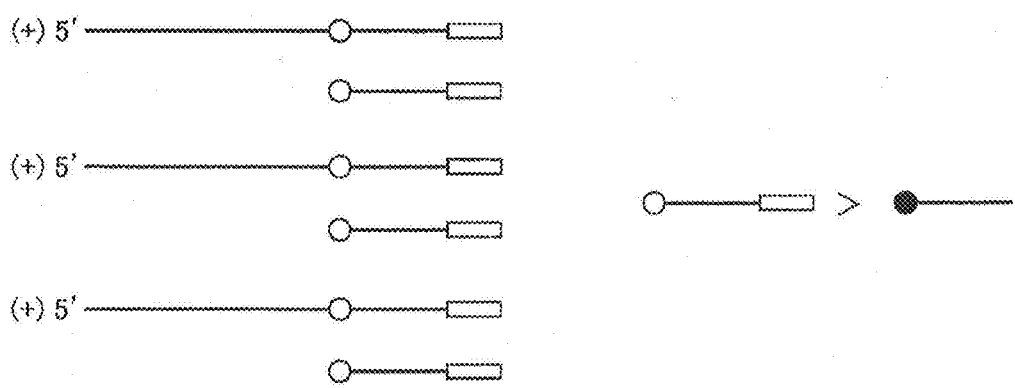

Next, annealing of the normal primer ($X1_{wt}$) and the mutant primer ($X2_{mt}$), and extended strands generated from these primers will be described. When only the normal template (+) is present as a template nucleic acid, the normal primer ($X1_{wt}$) is more likely to anneal to the normal template primer ($X1_{wt}$) than the mutant primer ($X2_{mt}$) (FIG. 2A). From the normal primer ($X1_{wt}$) that has annealed to the normal template (+), a normal extended strand (−) including a normal target site is generated. The normal primer ($X1_{wt}$) has, in its 5' region, an additional sequence (E1) noncomplementary to the template. Thus, the normal extended strand (−) has an additional sequence (E1) in its 5' region. Subsequently, based on this normal extended strand (−), a normal extended strand (+) complementary to the normal extended strand (−) is generated by a forward primer (FIG. 2B). Since this normal extended strand (+) is complementary to the normal extended strand (−), it has a sequence (E1') complementary to the additional sequence (E1) in its 3' region. Therefore, as shown in FIG. 2C, the normal primer ($X1_{wt}$) anneals to the normal extended strand (+) with a higher affinity than the mutant primer ($X2_{mt}$). This is because the mutant primer ($X2_{mt}$) shows a mismatch to the target site ($x_{wt}$) and does not have a sequence (E1) complementary to the sequence (E1'), whereas the normal probe ($X1_{wt}$) shows a match to the target site ($x_{wt}$) and has the sequence (E1) complementary to the sequence (E1). Thus, when the normal primer ($X1_{wt}$) has the additional sequence (E1), the normal extended strand (+) as the forward strand includes the sequence (Er) without fail. Thus, annealing of the normal primer ($X1_{wt}$) to the normal extended strand (+) occurs preferentially, whereby the annealing of the mutant primer ($X2_{mt}$) to the same is inhibited sufficiently. Therefore, according to the present invention, for example, amplification caused by erroneous annealing of a mutant primer can be prevented, thereby allowing the occurrence of false positives in polymorphism detection to be inhibited sufficiently. Although the above description is directed to an example where the first base (x1) is a normal base ($x_{wt}$) and the second base (x2) is a mutant base ($x_{mt}$), the present invention is by no means limited to this example, as will be described below.

As described above, according to the present invention, by the presence of the additional sequence (E1) in the primer (X1), it is possible to inhibit erroneous amplification of a target sequence including a non-existent polymorphic base. Thus, it is preferable that a polymorphic base whose erroneous amplification causes a false positive and thus is desired to be prevented is set to the second base (x2). It is preferable that the other polymorphic base that does not cause a false positive is then set to the first base (x1). The base at the target site (x) may be, for example, a normal base ($x_{wt}$) and a mutant base ($x_{mt}$), as described above. In this case, either of the first base (x1) and the second base (x2) may be a normal base ($x_{wt}$) or a mutant base ($x_{mt}$). In the field of clinical practice, as described above, a gene generally has a normal base at the target site showing a polymorphism. Thus, determination as to whether or not a gene including a mutant base is present is very important. Accordingly, even when only the normal gene is present, if amplification of a mutant target sequence is observed, it is interpreted that a mutant gene is present, resulting in a false positive. Therefore, in the present invention, it is preferable to prevent erroneous amplification of a mutant target sequence including a mutant base, for example. Thus, it is preferable to set the first base (x1) to a normal base ($x_{wt}$), the primer (X1) to a normal primer ($X1_{wt}$), the second base (x2) to a mutant base ($x_{mt}$), and the primer (X2) to a mutant primer ($X2_{mt}$). It is to be noted that, however, that the present invention is not limited thereto. For example, when a plurality of mutant bases ($x_{mt}$) are present at the target site, any two kinds of the mutant bases ($x_{mt}$) may be used as bases at the target site in the template nucleic acid, for example.

In the present invention, the primer (X1) has the sequence (A1') in its 3' region, so that, for example, the 3' end of the sequence (A1') is the 3' end of the primer (X1). Furthermore, the primer (X2) has the sequence (A2') in its 3' region, so that, for example, the 3' end of the sequence (A2') is the 3' end of the primer (X2).

As described above, the sequence (A1') of the primer (X1) is complementary to the partial sequence (A1) of the template nucleic acid, and has, in its 3' region, the base (x1') complementary to the first base (x1) at the target site in the 5' region of the partial sequence (A1). Furthermore, as described above, the sequence (A2') of the primer (X2) is complementary to the partial sequence (A2) in the template nucleic acid, and has, in its 3' region, the base (x2') complementary to the second base (x2) at the target site in the 5' region of the partial sequence (A2). In the present invention, "complementary bases" means, for example, bases that are bound to each other via a hydrogen bond or the like when they form a double-stranded nucleic acid, such as adenine and thymine or uracil, and guanine and cytosine. Furthermore, in the present invention, "a sequence complementary to a partial sequence" means that the sequence can anneal to the partial sequence as a whole, for example. Thus, the sequence is not necessarily a sequence consisting of bases perfectly complementary to the partial sequence, and may be a sequence including one or more bases noncomplementary to the partial sequence. Hereinafter, the sequence consisting only of perfectly complementary bases is referred to as a "perfect match sequence or full match sequence", and the sequence including a noncomplementary base(s) is referred to as a "mismatch sequence". Examples of the mismatch sequence include sequences in which one or more bases, excluding the base complementary to the target site, are deleted, substituted, added, or inserted as compared with the perfect match sequence, for example, and such a base(s) is referred to as a "mismatch base". The number of the mismatch bases is not particularly limited as long as the mismatch sequence can anneal to the partial sequence, and is, for example, 1 to 30, preferably 1 to 5. Furthermore, the proportion of the number of the mismatch bases in the base length of the sequence (A1') or the sequence (A2') is not particularly limited, and is, for example, 60% or less, preferably 10% or less. In particular, the sequence (A1') of the primer (X1) preferably is a perfect match sequence to the partial sequence (A1), and the sequence (A2') of the primer (X2) preferably is a perfect match sequence to the partial sequence (A2).

In the present invention, the prevention of the above-described erroneous annealing of a primer can be realized with high reliability by the presence of the additional sequence (E1) in the primer (X1). This is effective particularly in the case where, among a template nucleic acid in which the target site is the first base (x1) and a template nucleic acid in which the target site is the second base (x2), only the former is contained in a sample. On the other hand, in the case where the sample contains not only the template nucleic acid in which the target site is the first base (x1) but also the template nucleic acid in which the target site is the second base (x2), not only a target sequence including the first base (x1) but also a target sequence including the second base (x2) is amplified. Thus, when the sample contains the template nucleic acid in which the target site is the first base (x1) and the template nucleic acid in which the target site is the second base (x2) as described above, it is preferable to amplify the target sequence including the second base (x2) more preferentially than the target sequence including the first base (x1). Specifically, for example, it is preferable to amplify a target sequence including a mutant base as the second base (x2) more preferentially than a target sequence including a normal base as the first base (x1). As described above, since a polymorphism can serve as an indicator of diseases such as cancers, it is required to detect whether a target site is a normal base or a mutant base with high sensitivity. For example, in the case of a cancer, a collected biological sample, such as a piece of tissue, contains not only cancer cells but also a large number of normal cells. Thus, it is required to amplify target sequences included in a small amount of cancer cell-derived template nucleic acids in the collected piece of tissue more efficiently than those in a large number of normal cell-derived template nucleic acids. Furthermore, in an early stage of a disease, the amount of normal template nucleic acids is much larger than the amount of mutant template nucleic acids in a biological sample, for example. Thus, also in such a case, it is required to amplify a mutant target sequence efficiently, similarly to the above. Thus, in the present invention, for example, it is preferable that: a primer for amplifying a template contained at a relatively high proportion, such as a normal gene, is set to the primer (X1); a primer for amplifying a template contained at a relatively low proportion, such as a mutant gene, is set to the primer (X2); and the sequence (A1') of the primer (X1) and the sequence (A2') of the primer (X2) are set as follows. This allows the target sequence including the second base (x2) to be amplified more preferentially than the target sequence including the first base (x1).

The sequence (A1') of the primer (X1) is a region that anneals to the partial sequence (A1), and the sequence (A2') of the primer (X2) is a region that anneals to the partial sequence (A2). In the present invention, it is preferable to set the affinity, i.e., ease of annealing, of the sequence (A2') of the primer (X2) for the perfect match sequence thereto higher than that of the sequence (A1') of the primer (X1) for the perfect match sequence thereto, for example.

The adjustment of the affinities of the respective primers is not particularly limited, and can be achieved by setting the Tm values of the primers, for example. In the present invention, for example, it is preferable that the Tm value of a hybrid of the sequence (A2') of the primer (X2) with the perfect match sequence thereto is relatively higher than the Tm value of a hybrid of the sequence (A1') of the primer (X1) with the perfect match sequence thereto. By setting the Tm value of the sequence (A2') of the primer (X2) higher than the Tm value of the sequence (A1) of the primer (X1) as described above, it is possible to improve the binding property of the sequence (A2') of the primer (X2) to a template nucleic acid including the second base (x2) and an extended strand including the second base (x2) as compared with the binding property of the sequence (A1') of the primer (X1) to a template nucleic acid including the first base (x1) and an extended strand including the first base (x1), for example. As a result, the amplification efficiency of a target sequence including the first base (x1) by the primer (X1) can be improved as compared with the amplification efficiency of a target sequence including the second base (x2) by the primer (X2). By improving the amplification efficiency as described above, for example, even in the case where the content of the template nucleic acid in which the target site is the second base (x2) in a sample is low, a sufficient amount of amplification products of a target sequence including the second base (x2) can be obtained. Thus, the polymorphism of the second base (x2) also can be detected with a sufficient sensitivity in Tm analysis.

The difference between the Tm value of the sequence (A1') of the primer (X1) and the Tm value of the sequence (A2') of the primer (X2) is not particularly limited. For example, the difference preferably is more than 0° C. but not more than 20° C., more preferably more than 0° C. but not more than 10° C., and particularly preferably more than 0° C. but not more than 5° C.

The method for setting the Tm value of each of the sequence (A1') of the primer (X1) and the sequence (A2') of the primer (X2) is not particularly limited. The Tm value can be adjusted by, for example, adjusting the length of each of the sequences (A1') and (A2'), the GC content in each sequence, and the like. When the Tm value is adjusted by adjusting the length, the Tm value generally can be set relatively high as the length becomes relatively long. In the present embodiment, for example, it is preferable to set the sequence (A2') of the primer (X2) to be longer than the sequence (A1') of the primer (X1). This allows the Tm value of the sequence (A2') of the primer (X2) to be set relatively higher than the Tm value of the sequence (A1') of the primer (X1). Furthermore, when the Tm value is adjusted by adjusting the GC content, the Tm value can be set relatively high as the GC content becomes relatively high, for example. In the present embodiment, it is preferable to set the GC content in the sequence (A2') of the primer (X2) to be higher than the GC content in the sequence (A1') of the primer (X1), for example. Also, the Tm value may be adjusted by adjusting both the length and the GC content regarding each of the sequences (A1') and (A2'). Other than the above methods, by designing the sequence so as to include, for example, LNA as an RNA analog, PNA as a peptide nucleic acid, BNA as a cross-linked nucleic acid, or the like, it is possible to set the Tm value relatively higher than the Tm value of a sequence without them, for example.

When the sequence (A2') of the primer (X2) is set to be longer than the sequence (A1') of the primer (X1), the difference in length between these sequences is not particularly limited, and is, for example, more than 0 but not more than 20 bases, preferably more than 0 but not more than 10 bases, and more preferably more than 0 but not more than 5 bases.

Furthermore, for example, an extension reaction of the primer (X2) that has annealed to the partial sequence (A2) including the second base (x2) may be adapted to occur more likely than an extension reaction of the primer (X1) that has annealed to the partial sequence (A1) including the first base (x1). This allows the target sequence including the second base (x2) to be amplified more preferentially than the target sequence including the first base (x1), for example. The reactivity of the extension reaction from the primer can be adjusted, and the method thereof is not particularly limited. For example, it can be carried out by a known method. Specific examples of the method include: adding substances such as a fluorescent substance and biotin to the 5' region of the primer (X2); and adding an additional sequence to the same. These methods can be carried out based on the description in JP 2004-337124 A and the like, for example.

The primer (X1) is not limited as long as it has, in the 3' region of the sequence (A1'), the base (x1') complementary to the first base (x1). Preferably, in the sequence (A1'), at least one of the 1st base and the 2nd base from the 3' end is the base (x1') complementary to the first base (x1). More preferably, in the sequence (A1'), the base at the 3' end is the base (x1'). For example, it is assumed that the sequence of the template nucleic acid is "5'-...acGtt...-3'", and the first base (x1) is a base indicated with a capital letter "G". In this case, the primer (X1) can be designed so as to have a sequence "5'-...aaC-3'" where the 1st base from the 3' end is a base (C) complementary to the first base (x1=G). Also, the primer (X1) may be designed so as to have a sequence "5'-...aaCg-3'" where the 2nd base from the 3' end is a base (C) complementary to the first base (x1=G), for example.

In the former case, it is preferable that the 1st base from the 3' end is set to the base (x1') complementary to the first base (x1), and further, at least one base selected from the 2nd base from the 3' end to the base at the 5' end is set to a base that shows a mismatch to the template nucleic acid. In particular, it is preferable that at least one of the 2nd base and the 3rd base from the 3' end, more preferably the 2nd base from the 3' end is set to a base that shows a mismatch to the template nucleic acid. For example, as in the above, it is assumed that the sequence of the template nucleic acid is "5'-...acGtt...-3'", and the first base (x1) is a base indicated with a capital letter "G". In this case, the primer (X1) may be designed so as to have a sequence "5'-...atC-3'" where the 1st base from the 3' end is a base (C) complementary to the first base (x1=G), and the 2nd base from the 3' end is a base (t) that shows a mismatch to the underlined base (t) of the template nucleic acid, instead of a base (a) complementary to the underlined base (t). Furthermore, in the latter case, it is preferable that the 2nd base from the 3' end is set to the base (x1') complementary to the first base (x1), and further, the 1st base from the 3' end and/or at least one base selected from the 3rd base from the 3' end to the base at the 5' end is set to a base that shows a mismatch to the template nucleic acid. In particular, it is preferable that at least one of the 1st base and the 3rd from the 3' end, more preferably the 3rd base from the 3' end is set to the mismatch base. For example, as in the above, it is assumed that the sequence of the template nucleic acid is "5'-...acGtt...-3'", and the first base (x1) is a base indicated with a capital letter "G". In this case, the primer (X1) may be designed so as to have a sequence "5'-...atCg-3'" where the 2nd base from the 3' end is a base (C) complementary to the first base (x1=G), and the 3rd base from the 3' end is a base (t) that shows a mismatch to the underlined base (t), instead of a base (a) complementary to the underlined base (t). As described above, by designing the primer (X1) so that the sequence (A1') includes a mismatch base, it is possible to further improve the specificity of the primer (X1) to a sequence including the first base (x1).

The primer (X2) is not limited as long as it has, in the 3' region of the sequence (A2'), the base (x2') complementary to the second base (x2). Preferably, in the sequence (A2'), at least one of the 1st base and the 2nd base from the 3' end is the base (x2') complementary to the second base (x2). More preferably, in the sequence (A2'), the base at the 3' end is the base (x2'). For example, it is assumed that the sequence of the template nucleic acid is "5'-...acAtt...-3'", and the second base (x2) is a base indicated with a capital letter "A". In this case, the primer (X2) can be designed so as to have a sequence "5'-...aaT-3'" where the 1st base from the 3' end is a base (C) complementary to the second base (x2=A). Also, the primer (X2) may be designed so as to have a sequence "5'-...aaTg-3'" where the 2nd base from the 3' end is a base (T) complementary to the second base (x2=A), for example.

In the former case, it is preferable that the 1st base from the 3' end is set to the base (x2') complementary to the second base (x2), and further, at least one base selected from the 2nd base from the 3' end to the base at the 5' end is set to a base that shows a mismatch to the template nucleic acid. In particular, it is preferable that at least one of the 2nd base and the 3rd base from the 3' end, more preferably the 2nd base from the 3' end is set to a base that shows a mismatch to the template nucleic acid. For example, as in the above, it is assumed that the sequence of the template nucleic acid is "5'-...acAtt...-3'", and the second base (x2) is a base indicated with a capital letter "A". In this case, the primer (X2) may be designed so as to have a sequence "5'- . . . atT-3'" where the 1st base from the 3' end is a base (T) complementary to the second base (x2=A), and the 2nd base from the 3' end is a base (t) that shows a mismatch to the underlined base (t) of the template nucleic acid, instead of a base (a) complementary to the underlined base (t). Furthermore, in the latter case, it is preferable that the 2nd base from the 3' end is set to the base (x2') complementary to the second base (x2), and further, the 1st base from the 3' end and/or at least one base selected from the 3rd base from the 3' end to the base at the 5' end is set to a base that shows a mismatch to the template nucleic acid. In particular, it is preferable that at least one of the 1st base and the 3rd from the 3' end, more preferably the 3rd base from the 3' end is set to the mismatch base. For example, as in the above, it is assumed that the sequence of the template nucleic acid is "5'- . . . acA tt . . . -3'", and the second base (x2) is a base indicated with a capital letter "A". In this case, the primer (X2) may be designed so as to have a sequence "5'- . . . atTg-3'" where the 2nd base from the 3' end is a base (T) complementary to the second base (x2=A), and the 3rd base from the 3' end is a base (t) that shows a mismatch to the underlined base (t) of the template nucleic acid, instead of a base (a) complementary to the underlined base (t). As described above, by designing the primer (X2) so as to include a mismatch base, it is possible to further improve the specificity of the primer (X2) to a sequence including the second base (x2).

In the present invention, the additional sequence (E1) of the primer (X1) is, as described above, an additional sequence noncomplementary to the partial sequence (B1) adjacent to the 3' end of the partial sequence (A1) in the template nucleic acid, and is bound to the 5' end of the sequence (A1'). In the present invention, "a sequence noncomplementary to a partial sequence" means a sequence that cannot anneal to the partial sequence, for example (the same applied hereinafter). The complementarity between the partial sequence (B1) of the template nucleic acid and the additional sequence (E1), for example, when they are aligned is preferably 90% or less, more preferably 50% or less, still more preferably 10% or less, and particularly preferably 0%, i.e., the additional sequence (E1) consists only of bases perfectly noncomplementary to the partial sequence (B1).

The base length of the additional sequence (E1) is not particularly limited, and is, for example, 1 to 50-mer, preferably 1 to 20-mer, and more preferably 1 to 10-mer. The base length of the additional sequence (E1) is, for example, 1/50 to 1/1, preferably 1/20 to 1/1, and more preferably 1/10 to 1/2 of the base length of the sequence (A1') of the primer (X1), for example.

In the present invention, the primer (X2) may further include a sequence (E2). The sequence (E2) is noncomplementary to a partial sequence (B2) adjacent to the 3' end of the partial sequence (A2). The sequence (E2) also is referred to as an additional sequence, for example.

The primer (X2) is schematically shown in FIG. 1B. FIG. 1B is a schematic view showing the relationship between a template and the primer (X2). As shown in FIG. 1B, in the sequence of the template (+), a sequence having the base (x2) at the target site in its 5' region is previously determined as a partial sequence (A2), and a sequence adjacent to the 3' end of the partial sequence (A2) is previously determined as a partial sequence (B2). On the other hand, the primer (X2) is configured so that it includes a sequence (A2') complementary to the partial sequence (A2) and a sequence (E2) noncomplementary to the partial sequence (B2). The additional sequence (E2) is bound to the 5' end of the sequence (A2'). In the primer (X2), a complementary base (x2') to be paired with the second base (x2) at the target site is located in a 3' region of the sequence (A2').

Preferably, the additional sequence (E2) is different from the additional sequence (E1). By the presence of the additional sequence (E2) in the primer (X2), the specificity of the primer (X2) to a sequence including the second base (x2) can be improved, for example. As a result, a target sequence in which the target site is the second base (x2) can be amplified with higher amplification efficiency.

Figure 3A:
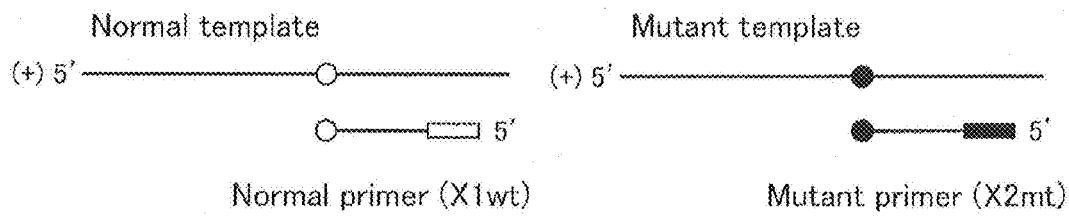
FIG. 3 shows schematic views showing another example of annealing of the primers of the present invention and extended strands resulting therefrom.
Figure 3B:
Figure 3C:
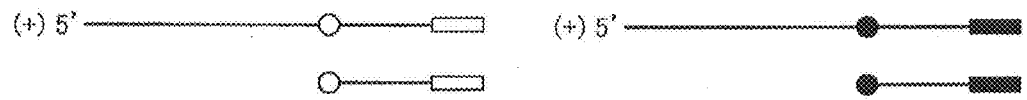

When the primer (X2) has the additional sequence (E2), an amplification reaction caused the primer (X2) is as shown in FIG. 3, for example. FIG. 3 shows schematic views showing, when the primer (X1) having the additional sequence (E1) and the primer (X2) having the additional sequence (E2) are used, annealing of each of these primers to a template nucleic acid and to an extended strand. Although FIG. 3 is directed to an example where the primer (X1) is a normal primer ($X1_{wt}$) and the primer (X2) is a mutant primer ($X2_{mt}$), the present invention is not limited thereto, as described above.

FIG. 3 shows schematic views showing, when the primer (X1) having the additional sequence (E1) and the primer (X2) having the additional sequence (E2) are used in the present invention, the state of the annealing of each of these primers. When both the normal template (+) and the mutant template (+) are contained in a sample, generally, the normal primer ($X1_{wt}$) is more likely to anneal to the normal template (+), whereas the mutant primer ($X2_{mt}$) is more likely to anneal to the mutant template (+) (FIG. 3A). The normal primer ($X1_{wt}$) having annealed to the normal template (+) has the additional sequence (E1). Thus, a normal extended strand (−) generated from the normal primer ($X1_{wt}$) has the additional sequence (E1) on the 5' side. On the other hand, the mutant primer ($X2_{mt}$) having annealed to the mutant template (+) has the additional sequence (E2). Thus, a mutant extended strand (−) generated from the primer ($X2_{mt}$) has the additional sequence (E2) on the 5' side. Thus, a complementary normal extended strand (+) generated by a forward primer based on the normal extended strand (−) has a sequence (E1') complementary to the additional sequence (E1), and a complementary mutant extended strand (+) generated based on the mutant extended strand (−) has a sequence (E2') complementary to the additional sequence (E2) (FIG. 3B). Further, since the additional sequence (E1) of the normal primer ($X1_{wt}$) and the additional sequence (E2) of the mutant primer ($X2_{mt}$) are different from each other, the normal primer ($X1_{wt}$) having the additional sequence (E1) specifically anneals to the normal extended strand (+), and the mutant primer ($X2_{mt}$) having the additional sequence (E2) specifically anneals to the mutant extended strand (+). Therefore, a normal extended strand is amplified by the normal primer ($X1_{wt}$) with excellent amplification efficiency, and a mutant extended strand is amplified by the mutant primer ($X2_{mt}$) with excellent amplification efficiency. At this time, for example, by setting the sequence (A1') of the primer (X1) and the sequence (A2') of the primer (X2) so as to satisfy the above-described relationship, it is possible to cause the amplification by the primer (X2) more preferentially than the amplification by the primer (X1). Although the description is made here with reference to an example where the first base (x1) is a normal base ($x_{mt}$) and the second base (x2) is a mutant base ($x_{mt}$), the present invention is by no means limited to this example, as described above.

The additional sequence (E2) of the primer (X2) is noncomplementary to the partial sequence (B2) of the template nucleic acid, as described above, for example. The complementarity between the partial sequence (B2) of the template nucleic acid and the additional sequence (E2), for example, when they are aligned is preferably 90% or less, more preferably 50% or less, still more preferably 10% or less, and particularly preferably 0%, i.e., the additional sequence (E2) consists only of bases perfectly noncomplementary to the partial sequence (B2).

The additional sequence (E1) of the primer (X1) and the additional sequence (E2) of the primer (X2) are, for example, different from each other, as described above. The homology between the additional sequence (E1) and the additional sequence (E2), for example, when they are aligned is preferably 90% or less, more preferably 50% or less, still more preferably 10% or less, and particularly preferably 0%.

The base length of the additional sequence (E2) is not particularly limited, and is, for example, 1- to 50-mer, preferably 1- to 20-mer, and more preferably 1- to 10-mer. The base length of the additional sequence (E2) is, for example, 1/50 to 1/1, preferably 1/20 to 1/1, and more preferably 1/10 to 1/2 of the base length of the sequence (A2') of the primer (X2), for example. The additional sequence (E2) preferably has the same base length as the additional sequence (E1) of the primer (X1), for example.

The base length of each of the primers (X1) and (X2) is not particularly limited. The primer (X1) is, for example, 10- to 50-mer, preferably 15- to 45-mer, and more preferably 16- to 40-mer. The primer (X2) is, for example, 10- to 50-mer, preferably 15- to 45-mer, and more preferably 16- to 40-mer. As a specific example, when the primer (X2) consists only of the sequence (A2'), for example, the primer (X2) is, for example, 10- to 50-mer, preferably 15- to 40-mer, and more preferably 16- to 35-mer. When the primer (X2) includes, for example, the sequence (A2') and the additional sequence (E2), the primer (X2) is, for example, 10- to 50-mer, preferably 15- to 40-mer, and more preferably 16- to 35-mer.

Figure 1C:
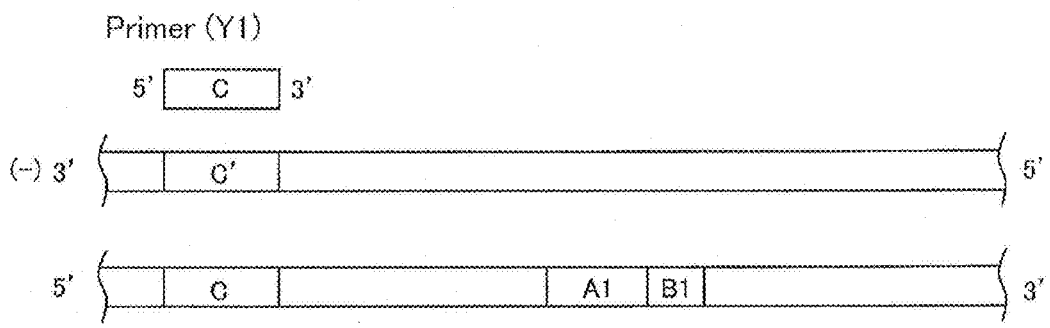

In the present invention, in the amplification step, for example, the following primer (Y1) further may be used in addition to the primers (X1) and (X2).
Primer (Y1): a primer including a partial sequence (C) that is located on the 5' side with respect to the target site in the template nucleic acid The primer (Y1) is schematically shown in FIG. 1C. FIG. 1C is a schematic view showing the relationship between a template and the primer (Y1). As shown in FIG. 1C, in the template, a partial sequence located on the 5' side with respect to the target site included in the partial sequence (A1) is determined as a sequence (C). On the other hand, the primer (Y1) is configured so that it includes the above-described partial sequence (C). A reverse strand (−) as a complementary strand to a forward strand (+) has a sequence (C') complementary to the partial sequence (C). Thus, the sequence (C) of the primer (Y1) anneals to the sequence (C') of the reverse strand (−), so that the primer (Y1) can amplify the forward strand.

The primer (Y1) is, for example, a forward primer for extending a forward strand, whereas the primers (X1) and (X2) are primers for extending a reverse strand. Thus, for example, the primer (Y1) as a forward primer can form a primer pair with each of the primers (X1) and (X2) as reverse primers. Furthermore, since the primer (Y1) anneals to a region different from the target site, it can amplify the target sequence regardless of the kind of the base at the target site, for example.

The length of the primer (Y1) is not particularly limited. In general, the length of the primer (Y1) preferably is 10- to 50-mer, more preferably 15- to 40-mer, and particularly preferably 16- to 35-mer. The primer (Y1) is not limited as long as it has the partial sequence (C) that is located on the 5' side with respect to the target site in the template nucleic acid.

The primer (Y1) may have an additional sequence on its 5' side, for example. It is preferable that the additional sequence is different from a sequence on the 5' side with respect to the partial sequence (C) in the template, for example.

In the amplification method of the present invention, in the amplification step, for example, a probe that can hybridize to a sequence including the target site in the template nucleic acid further may be added to the reaction system. The probe may be a labeled probe having a labeling substance, for example.

In the present invention, for example, amplification can be performed using, as a template nucleic acid, either of a single-stranded nucleic acid and a double-stranded nucleic acid. When the latter double-stranded nucleic acid is used, for example, amplification may be performed using two complementary single strands of this nucleic acid respectively as templates. When the template nucleic acid is a double-stranded nucleic acid, for example, a target site in the (+) strand and a target site in the (−) strand are to be paired with each other. The probe to be used in the polymorphism detection method of the present invention to be described below may be a probe that can hybridize to the (+) strand or a probe that can hybridize to the (−) strand, for example.

The template nucleic acid may be a single-stranded nucleic acid or a double-stranded nucleic acid, as described above. Examples of the template nucleic acid include DNAs and RNAs such as total RNA and mRNA.

The template nucleic acid may be a nucleic acid in a sample or an amplification product of the nucleic acid, for example. It may be a nucleic acid contained in a sample such as a biological sample. The former may be a nucleic acid inherently contained in a biological sample, for example. The latter is preferable because it allows the detection accuracy to be improved, for example. The amplification product can be prepared by amplifying a nucleic acid in the sample as a template according to a nucleic acid amplification method, for example. The amplification product may be an amplification product obtained by using DNA in the sample as a template or an amplification product obtained by using cDNA synthesized from RNA in the sample as a template, for example. Examples of the RNA in the sample include RNAs such as total RNA and mRNA, and the cDNA can be synthesized from the RNA such as described above by RT-PCR (Reverse Transcription PCR), for example. The length of the amplification product is not particularly limited, and is, for example, 50 to 1000 bp, preferably 80 to 200 bp.

In the present invention, in the amplification step, it is preferable to carry out an amplification reaction using a nucleic acid in a sample as a template. The sample is not particularly limited as long as it contains a nucleic acid that serves as a template. For example, the sample may be a sample containing a nucleic acid derived from a biological sample. Examples of the biological sample include: whole blood; blood cells such as leukocyte cells; bone marrow; oral cells such as oral mucosa; somatic cells such as cells of a nail and cells of a hair; germ cells; sputum; amniotic fluid; paraffin-embedded tissues; urine; gastric juice; liquid obtained by gastrolavage; and suspensions thereof. Furthermore, as described above, a reaction solution obtained after carrying out nucleic acid amplification using a nucleic acid derived from a biological sample as a template may be used as a nucleic acid sample in the present invention, and an amplification product contained in the reaction solution may be used as a template nucleic acid. According to the present invention, as described above, erroneous annealing of a primer can be inhibited regardless of whether a sample is purified or not. Thus, the present invention is particularly advantageous when applied to an unpurified sample. According to the method that allows the use of an unpurified sample as described above, a pretreatment for purifying the sample can be omitted, so that the method can be carried out still more easily and at a lower cost.

When the amplification method of the present invention is applied to the polymorphism detection method of the present invention to be described below, the sample is not particularly limited. For example, the polymorphism detection method is particularly effective when applied to a sample containing a nucleic acid in which it is unknown whether the base at the target site is mutant or normal, a sample containing both a nucleic acid with a mutant base and a nucleic acid with a normal base, a sample that might contain both of these nucleic acids, and the like. Substances from which the nucleic acids such as the above-described DNAs and RNAs are derived are not limited, and examples thereof include: cells such as various cancer cells; viruses; and mitochondria. In cells, such as blood cells, that have become cancerous include cells containing mutant nucleic acids and cells containing normal nucleic acids, so that the above-described problems are likely to occur. Therefore, the polymorphism detection method of the present invention preferably is applied to a sample containing a mutant nucleic acid and a normal nucleic acid, in particular. For example, it is preferable to apply the polymorphism detection method to biological samples such as various cancer cells like leukemia cells. Specifically, the polymorphism detection method preferably is applied to a blood sample, leukocyte cells, and the like. In the present invention, a method for collecting a sample, a method for preparing a nucleic acid, and the like are not limited, and conventionally known methods can be employed.

A nucleic acid derived from the biological sample can be isolated from the biological sample by a conventionally known method, for example. Isolation of genomic DNA from whole blood can be achieved using a commercially available genomic DNA isolation kit (GFX Genomic Blood DNA Purification Kit™; GE Healthcare Bio-Sciences) or the like, for example.

In the amplification step of the present invention, amplification in the same reaction system may be, for example, amplification of a target sequence in a single reaction solution.

The amplification method of the present invention is characterized in that the above-described primers are used in the amplification step, and other steps, conditions, and the like are by no means limited. A nucleic acid amplification method to be used in the amplification step is not particularly limited, and examples thereof include a PCR (Polymerase Chain Reaction) method, a NASBA (Nucleic Acid Sequence Based Amplification) method, a TMA (Transcription-Mediated Amplification) method, and a SDA (Strand Displacement Amplification) method. Among them, the PCR method is preferable. The conditions of the nucleic acid amplification method are not particularly limited, and the method can be carried out using conventionally known techniques.

In the amplification step, the proportion of the added nucleic acid sample in a reaction system (e.g., a reaction solution) of an amplification reaction is not particularly limited. When the nucleic acid sample is a biological sample (e.g., a whole blood sample), the lower limit of the proportion of the added biological sample in the reaction system preferably is 0.01 vol %, more preferably 0.05 vol %, and still more preferably 0.1 vol %, for example. Also, the upper limit of the same is not particularly limited, and preferably is 2 vol %, more preferably 1 vol %, and still more preferably 0.5 vol %, for example.

Furthermore, for example, when optical detection using a probe is carried out in the detection of a mutation to be described below, the proportion of the added biological sample (e.g., whole blood sample) in the reaction system preferably is set to 0.1 to 0.5 vol %, for example. In a PCR reaction, a heat treatment generally is performed for denaturation of DNA (dissociation into single-stranded DNAs). However, by this heat treatment, sugars, proteins, and the like contained in the sample may be denatured, so that precipitates, turbidity, or the like may be generated owing to insolubilization of these components. Thus, when the presence or absence of mutation is examined by an optical method, the generation of such precipitates or turbidity may influence the measurement accuracy. However, by setting the proportion of the added biological sample in the reaction system within the above-described range, for example, the influence by the generation of the precipitates or the like caused by the denaturation can be prevented sufficiently, although the mechanism thereof is unknown. Thus, the measurement accuracy by the optical method can be improved. Moreover, interference with the PCR by contaminants in the biological sample also is inhibited sufficiently, so that the amplification efficiency can be improved still further. Therefore, by setting the proportion of the added biological sample such as a whole blood sample within the above-described range, it becomes possible to eliminate the necessity of pretreating the sample to prevent the generation of precipitates or turbidity or to remove them, for example.

Furthermore, the proportion of the whole blood sample in the reaction system can also be represented by percent by weight of hemoglobin (hereinafter referred to as "Hb"), instead of percent by volume (e.g., 0.1 to 0.5 vol %) as in the above. In this case, the proportion of the whole blood sample in the reaction system is preferably 0.565 to 113 g/l, more preferably 2.825 to 56.5 g/l, and still more preferably 5.65 to 28.25 g/l, in terms of the amount of Hb, for example. The proportion of the added whole blood sample in the reaction system may satisfy both the above-described percent by volume and percent by weight of hemoglobin, or may satisfy either one of them, for example. Whole blood may be, for example, any of hemolyzed whole blood, non-hemolyzed whole blood, anticoagulated whole blood, and whole blood containing a coagulated fraction.

In the amplification step, it is preferable that albumin further is added to the reaction system before starting the amplification reaction. By the addition of albumin, for example, the above-described influence by the generation of precipitates or turbidity can be reduced still further and also the amplification efficiency can be further improved.

The proportion of the added albumin in the reaction system is, for example, 0.01 to 2 wt %, preferably 0.1 to 1 wt %, and more preferably 0.2 to 0.8 wt %. The albumin is not particularly limited, and examples thereof include bovine serum albumin (BSA), human serum albumin, rat serum albumin, and horse serum albumin. Only one kind of albumin may be used, or two or more kinds of albumin may be used in combination.

Next, the amplification method of the present invention will be described with reference to an example where amplification is carried out by the PCR method using a normal primer ($X1_{wt}$) as the primer (X1) and a mutant primer ($X2_{mt}$) as the primer (X2). It is to be noted, however, that the present invention is not limited thereto. Furthermore, conditions of the PCR are not particularly limited, and the PCR can be carried out by a conventionally known method.

First, a PCR reaction solution containing a template nucleic acid and the above-described respective primers is prepared. The proportion of each primer added in the PCR reaction solution is not particularly limited. The normal primer ($X1_{wt}$) preferably is added so that the concentration thereof is 0.01 to 10 μmol/l, more preferably 0.05 to 5 μmol/l, and particularly preferably 0.1 to 1 μmol/l, for example. The mutant primer ($X2_{mt}$) preferably is added so that the concentration thereof is 0.01 to 10 μmol/l, more preferably 0.05 to 5 μmol/l, and particularly preferably 0.1 to 0.5 μmol/l, for example. The molar ratio ($X1_{wt}$:$X2_{mt}$) between the normal primer ($X1_{wt}$) and the mutant primer ($X2_{mt}$) is preferably 0.001:1 to 10:1, more preferably 0.01:1 to 2:1, and particularly preferably 0.1:1 to 1:1, for example.

Furthermore, in the case where the primer (Y1) is used in addition to the normal primer ($X1_{wt}$) and the mutant primer ($X2_{mt}$), the primer (Y1) preferably is added so that the concentration thereof is 0.01 to 10 μmol/l, more preferably 0.05 to 5 μmol/l, and particularly preferably 0.1 to 1 μmol/l, for example. The molar ratio ($X2_{mt}$:Y1) between the mutant primer ($X2_{mt}$) and the primer (Y1) is preferably 1:0.001 to 1:10, more preferably 1:0.01 to 1:2, and particularly preferably 1:0.1 to 1:1, for example.

The reaction solution may further contain other components. For example, the reaction solution preferably contains components involved in a PCR reaction. The above-described other components are not particularly limited, and those skilled in the art can set the components as appropriate. Examples of the other components include: polymerases such as DNA polymerase; nucleoside triphosphate; solvents; and various kinds of catalysts. The order of adding the respective components to the reaction solution is by no means limited, for example.

The DNA polymerase is not particularly limited, and conventionally known polymerases derived from heat-resistant bacteria can be used, for example. As specific examples of such polymerases, *Thermus aquaticus*-derived DNA polymerases (U.S. Pat. Nos. 4,889,818 and 5,079,352) (Taq Polymerase™), *Thermus thermophilus*-derived DNA polymerase (WO 91/09950) (rTth DNA polymerase), *Pyrococcus furiosus*-derived DNA polymerase (WO 92/9689) (Pfu DNA polymerase: Stratagenes), *Thermococcus litoralis*-derived polymerase (EP-A 455 430 (Vent™): New England Biolabs), and the like are commercially available. Among them, heat-resistant DNA polymerase derived from *Thermus aquaticus* is preferable.

The proportion of the added DNA polymerase in the reaction solution is not particularly limited, and is, for example, 1 to 100 U/ml, preferably 5 to 50 U/ml, and more preferably 20 to 40 U/ml. With regard to the unit of activity (U) of DNA polymerases, 1 U generally is defined as an activity for incorporating 10 nmol of entire nucleotide into acid-insoluble precipitate at 74° C. in 30 minutes in a reaction solution for activity measurement using activated salmon sperm DNA as a template primer. The composition of the reaction solution for activity measurement is as follows, for example: 25 mmol/l TAPS buffer (pH 9.3, 25° C.), 50 mmol/l KCl, 2 mmol/l $MgCl_2$, 1 mmol/l mercaptoethanol, 200 μmol/l dATP, 200 μmol/l dGTP, 200 μmol/l dTTP, 100 μmol/l [$\alpha$-$^{32}$P] dCTP, and 0.25 mg/mL activated salmon sperm DNA.

The nucleoside triphosphate generally is dNTP (dATP, dCTP, dGTP, and dTTP or dUTP). The proportion of the added dNTP in the reaction solution is not particularly limited, and is, for example, 0.01 to 1 mmol/l, preferably 0.05 to 0.5 mmol/l, and more preferably 0.1 to 0.3 mmol/l.

Examples of the solvent include buffer solutions such as Tris-HCl, Tricine, MES, MOPS, HEPES, and CAPS, and it is possible to use commercially available buffer solutions for PCR and buffer solutions included in commercially available PCR kits.

The reaction solution further may contain heparin, betaine, KCl, $MgCl_2$, $MgSO_4$, glycerol, or the like, and the proportions of these components to be added may be set within ranges where they do not interfere with the PCR reaction.

The total volume of the reaction solution is not particularly limited, and can be determined as appropriate depending on a device to be used, such as a thermal cycler, and the like, for example. Generally, the total volume is 1 to 500 μl, preferably 10 to 100 μl.

Next, PCR is conducted. The PCR includes the following three steps: (1) dissociation of a double-stranded nucleic acid into single-stranded nucleic acids; (2) annealing of the primers; and (3) extension of the primers (a polymerase reaction). The conditions of the respective steps are not particularly limited. In the step (1), it is preferable to perform a treatment at 90° C. to 99° C. for 1 to 120 seconds, more preferably at 92° C. to 95° C. for 1 to 60 seconds, for example. In the step (2), it is preferable to perform a treatment at 40° C. to 70° C. for 1 to 300 seconds, more preferably at 50° C. to 70° C. for 5 to 60 seconds, for example. In the step (3), it is preferable to perform a treatment at 50° C. to 80° C. for 1 to 300 seconds, more preferably at 50° C. to 75° C. for 5 to 60 seconds, for example. The number of cycles is not particularly limited. It preferably is 30 cycles or more with the three steps (1) to (3) as one cycle, for example. The upper limit of the number of cycles is not particularly limited, and is, for example, 100 cycles or less in total, preferably 70 cycles or less in total, and more preferably 50 cycles or less in total. The temperature change in each step can be controlled automatically using a thermal cycler or the like, for example.

In the present invention, in a single reaction system, it is possible to amplify target sequences of two or more kinds of respective genes at the same time, for example. Also, it is possible to amplify two or more kinds of target sequences respectively including polymorphisms at different sites in the same gene. In this case, the above-described primers (X1) and (X2), and optionally the primer (Y1), are provided for each of the target sequences, and an amplification reaction such as described above may be performed in the presence of all these primers.

The method for amplifying a target sequence according to the present invention further may include the step of detecting an amplification product obtained through the above-described amplification reaction. With this configuration, it is possible to detect the polymorphism at the target site in the target sequence, for example. The above-described polymorphism detection can be achieved by, for example, Tm analysis to be described below. Specifically, a probe that can hybridize to the target sequence including the target site in the template sequence further is added to a reaction system of the amplification reaction in the amplification step, for example. Then, while changing the temperature of the reaction system, signal values indicating the melting states of a hybrid of the amplification product and the probe are measured. Thus, the kind of polymorphism such as mutant or normal can be checked based on the change in signal value accompanying the temperature change. The timing of adding the probe is not particularly limited. For example, the probe may be added to the reaction system before, during, or after the amplification reaction. In particular, it is preferable to add the probe before the amplification reaction, because, for example, it is not necessary to expose the reaction solution to the external environment in order to add the probe and it is possible to carry out the amplification reaction and the measurement of signal values successively. The polymorphism detection will be described specifically in the following description regarding the polymorphism detection method according to the present invention. The probe and the like also are as described below.

<Polymorphism Detection Method>

As described above, the polymorphism detection method according to the present invention includes the steps of amplifying a target sequence including a target site in a template nucleic acid by the amplification method according to the present invention; and detecting a polymorphism at the target site in the target sequence with a probe that can hybridize to the target sequence.

The present invention is characterized in that the target sequence is amplified by the above-described method, and polymorphism detection using the probe is performed with respect to the thus-obtained amplification product. Other steps, conditions, and the like are by no means limited.

The polymorphism detection method according to the present invention may include, for example, the following steps (a) to (c);

(a) amplifying the target sequence by the amplification method according to the present invention;

(b) while changing the temperature of the reaction system containing an amplification product obtained in the step (a) in the presence of the probe, measuring signal values indicating the melting states of a hybrid of the amplification product and the probe; and (c) detecting the polymorphism at the target site in the template nucleic acid based on change in signal value accompanying the temperature change.

The present invention preferably is applied to a sample containing a nucleic acid. The sample is not particularly limited, and examples thereof include those described above as examples of the sample. Furthermore, the kind of the template nucleic acid also is not particularly limited, and examples thereof include those described above as examples of the template nucleic acid.

The probe also is referred to as a "detection probe" hereinafter. The probe is not particularly limited, and can be set by a conventionally known method. For example, when the template nucleic acid is a double-stranded nucleic acid, the probe may be designed so as to hybridize to a sense strand of a target sequence (the probe is a sense strand detection probe), or may be designed so as to hybridize to an antisense strand of a target sequence (the probe is an antisense strand detection probe). At the time of designing the probe, a base at the target site in the target sequence may be set to either a normal base or a mutant base, for example. That is, the probe may be configured so that, for example, when the probe hybridizes to the target sequence, a base to be paired with the base at the target site in the target sequence is complementary to either a normal base or a mutant base, for example. In the present invention, for example, when a mutant gene is to be detected, the probe preferably is configured so that a base to be paired with the base at the target site is complementary to a mutant base and noncomplementary to a normal base.

In the present invention, the probe is not limited as long as it can hybridize to the target sequence including the target site, as described above. The sequence of the probe is not particularly limited. For example, when the probe forms a hybrid with the target sequence, it is preferable that the complementarity between the probe and the target sequence, excluding a base at a site to be paired with the target site, is, for example, 90% to 100%, particularly preferably 100%, i.e., the probe is a perfect match sequence to the target sequence.

The proportion of the added probe in the reaction system is not particularly limited. For example, it is preferable to add the probe so that the concentration thereof is in the range from 10 to 400 nmol/l, more preferably from 20 to 200 nmol/l. When the probe is a labeled probe labeled with a labeling substance such as a fluorescent dye, in order to adjust a signal intensity, such as a fluorescence intensity, to be detected, for example, an unlabeled probe having the same sequence as the labeled probe may be used in combination. This unlabeled probe may have a phosphate group added to its 3' end, for example. In this case, the molar ratio between the labeled probe and the unlabeled probe preferably is 1:10 to 10:1, for example. The length of the probe is not particularly limited, and is, for example, 5- to 50-mer, preferably 10- to 30-mer.

The probe may be added to the reaction system of the amplification reaction after the step (a), i.e., after the amplification reaction of the target sequence. However, it is preferable to add the probe to the reaction system prior to the amplification reaction in the step (a), because this allows the analysis to be conducted easily and rapidly. The proportion and the like of each of the probes added in the reaction system are as described above. In the case where the probe is added to the reaction system prior to the amplification reaction as described above, for example, in order to prevent the extension of the probe itself, a phosphate group further may be added to the 3' end of the probe, or the 3' end of the probe may be labeled with the above-described labeling substance.

The polymorphism detection method of the present invention can be utilized in so-called Tm analysis (also is referred to as "melting curve analysis") such as described above. The following is an explanation of a Tm value in the Tm analysis. For example, when a solution containing a double-stranded DNA is heated, an absorbance at 260 nm increases. This is because the hydrogen bond between the strands composing the double-stranded DNA is unbound by the heating, whereby the double-stranded DNA is dissociated into single-stranded DNAs (melting of DNA). Then, when every double-stranded DNA is dissociated into single-stranded DNAs, the absorbance of the solution becomes about 1.5 times as large as the absorbance at the time when the heating was initiated (i.e., the absorbance of the solution containing only the double-stranded nucleic acid), whereby it can be determined that the melting is completed. Based on this phenomenon, a melting temperature Tm generally is defined as a temperature at the time when the amount of increase in absorbance reaches 50% of the total amount of increase in absorbance.

In the step (b), the measurement of a signal value indicating the melting state of a hybrid of the amplification product and the probe may be the measurement of an absorbance at 260 nm as described above or the measurement of a signal of the labeling substance. Specifically, it is preferable that a labeled probe labeled with a labeling substance is used as the probe, and a signal of the labeling substance is measured. The labeled probe may be, for example, a labeled probe that shows signals independently and shows no signals when it forms a hybrid, or a labeled probe that shows no signals independently and shows signals when it forms a hybrid. The former probe does not show signals when it forms a hybrid (e.g., a double-stranded DNA) with the amplification product and shows signals when the probe is dissociated from the amplification product by heating. On the other hand, the latter probe shows signals when it forms a hybrid (e.g., a double-stranded DNA) with the amplification product, and the signals are reduced (quenched) when the probe is dissociated from the amplification product by heating. Therefore, by detecting signals of the labeling substance, it is possible to determine, for example, the progress of melting of the hybrid, the Tm value, and the like, as in the case where the absorbance at 260 nm is measured. The signal of the labeling substance may be detected under a condition specific to the signal of the labeling substance, for example. Examples of the condition include an excitation wavelength and a detection wavelength.

In the step (c), detection of the polymorphism at the target site based on the change in signal value can be carried out by a conventional method. Specifically, for example, by comparing the above-described change in signal value with the same regarding a hybrid of the probe and a mutant target sequence and/or a hybrid of the probe and a wild-type target sequence, it is possible to determine whether the polymorphism is mutant or wild-type. That is, the polymorphism can be determined as mutant when the change in signal value is the same as that of the hybrid with the mutant target sequence, whereas the polymorphism can be determined as wild-type when the change in signal value is the same as that of the hybrid with the wild-type target sequence. Alternatively, for example, the polymorphism can be determined by determining the Tm value based on the change in signal and then comparing the thus-determined Tm value with a Tm value as an evaluation standard. First, the Tm value is determined based on the change in signal value. Then, the measured Tm value is compared with a $Tm_{wt}$ value previously determined for the wild-type target sequence and/or a $Tm_{mt}$ value previously determined for the mutant target sequence. The polymorphism can be determined as: wild-type when the measured Tm value is the same as or similar to the $Tm_{wt}$ value as the evaluation standard; mutant when the measured Tm value is lower than the $Tm_{wt}$ value; mutant when the measured Tm value is the same as or similar to the $Tm_{mt}$ value as the evaluation standard; and wild-type when the measured Tm value is lower than the $Tm_{mt}$ value. Note here that the values "similar" to each other as used herein means values with difference of about ±3° C., for example.

Moreover, as described above, in the step (a), two or more kinds of target sequences can be amplified at the same time in the same reaction system. Then, polymorphisms at target sites of the respective amplification products can be determined. In this case, for each of the target sequences respectively including the target sites, a probe that hybridizes thereto may be provided. As the probes, it is preferable to use different labeled probes that are respectively labeled with labeling substances detectable under different conditions. By using such probes, even in the same reaction system, each of the polymorphisms can be detected by changing the detection condition.

In the labeled probe, a site to be labeled with the labeling substance is not particularly limited. In an oligonucleotide constituting the labeled probe, the site to be labeled preferably is located in a 5' region or a 3' region, more preferably at a position of the 1st to 4th bases from the 5' end or 3' end, more preferably, at a position of the 1st to 3rd bases from the 5' end or 3' end, and particularly preferably at a position of the 1st base (the base at the 5' end or 3' end) or the 2nd base from the 5' end or 3' end, for example. As will be described below, in the oligonucleotide, a base to be labeled with the labeling substance preferably is cytosine (c) or guanine (g), for example. The base may be labeled directly with the labeling substance, or alternatively, it may be labeled indirectly by labeling any site (e.g., phosphate group) in a nucleotide residue containing the base.

The labeling substance is not particularly limited, and preferably is the one that gives off signals depending on whether the labeled probe is present independently or it forms a hybrid, for example. The kind of the signal is not particularly limited, and examples of the signal include fluorescence, coloring, and color development. When the signal is fluorescence, examples of a signal value include a fluorescence intensity. When the signal is coloring or color development, examples of a signal value include reflectance, absorbance, and transmittance. The signal may be given off from the labeling substance directly or indirectly, for example.

The labeling substance is not particularly limited, and examples thereof include fluorescent substances such as a fluorophore. Examples of the fluorescent substance include fluorescein, phosphor, rhodamine, and polymethine dye derivatives. Examples of commercially available fluorescent substances include Pacific Blue® (Molecular Probes), BODIPY FL® (Molecular Probes), FluorePrime™ (Amersham Pharmacia), Fluoredite™ (Millipore Corporation), FAM® (ABI), Cy3™ and Cy5™ (Amersham Pharmacia), and TAMRA® (Molecular Probes). The detection condition for the fluorescent substance is not particularly limited, and can be determined as appropriate depending on the kind of the fluorescent substance to be used, for example. For example, Pacific Blue can be detected at a detection wavelength from 450 to 480 nm; TAMRA can be detected at a detection wavelength from 585 to 700 nm; and BODIPY FL can be detected at a detection wavelength from 515 to 555 nm. When such a probe is used, for example, by detecting fluorescence as a signal and measuring a fluorescence intensity as a signal value, hybridization and dissociation can be checked easily based on the change in fluorescence intensity.

Preferably, the labeled probe is, for example, a labeled probe that shows signals independently and shows no signals when it forms a hybrid, or a labeled probe that shows no signals independently and shows signals when it forms a hybrid. When the labeling substance is a fluorescent substance, the labeled probe preferably is a probe that is labeled with the fluorescent substance, shows fluorescence independently, and shows reduced (e.g., quenched) fluorescence when it forms a hybrid, for example. Such a phenomenon generally is called a fluorescence quenching phenomenon. Probes utilizing this phenomenon generally are called fluorescence quenching probes. Among these fluorescence quenching probes, preferred is the one in which the 3' end or the 5' end of the oligonucleotide is labeled with the fluorescent substance, and the base at the end to be labeled preferably is cytosine (c) or guanine (g). In the case where the base at the end is cytosine (c), the base sequence of the fluorescence quenching probe preferably is designed so that, for example, when the fluorescence quenching probe forms a hybrid with an amplification product, a base to be paired with the labeled cytosine (c) at the end or a base apart therefrom by one to three bases in the amplification product is guanine (g). A base away from the base to be paired with cytosine (c) by one base means a base located next to the base to be paired with cytosine (c). Such a probe generally is called a guanine quenching probe, and is known as a so-called QProbe®. When such a guanine quenching probe hybridizes to the amplification product, there occurs a phenomenon that, for example, as the fluorescent substance-labeled cytosine (c) at the end approaches guanine (g) in the amplification product, fluorescence of the fluorescent substance becomes weak (the fluorescence intensity is reduced). By using such a probe, hybridization and dissociation can be checked easily based on the change in fluorescence intensity. Similarly, in the case where the above-described base at the end is guanine (g), the base sequence of the fluorescence quenching probe preferably is designed so that, for example, when the fluorescence quenching probe forms a hybrid with an amplification product, a base to be paired with the labeled guanine (g) at the end or a base apart therefrom by one to three bases in the amplification product is cytosine (c).

In the probe, for example, a phosphate group may be added to the 3' end, as described above. As will be described below, at the time of an amplification reaction, the probe can be caused to be present in a reaction system of the amplification reaction. In such a case, when the 3' end of the probe has a phosphate group added thereto, it is possible to sufficiently prevent the probe itself from being extended by the amplification reaction. A similar effect is obtained also by adding a labeling substance such as described above to the 3' end of the probe.

Next, the polymorphism detection method of the present invention will be described with reference to an illustrative example where an amplification reaction is carried out by PCR, and a labeled probe is used as the detection probe. It is to be noted, however, that the present invention is not limited thereto.

First, using a reaction solution to which a sample containing a template nucleic acid, the above-described respective primers of the present invention, and a labeled probe that hybridizes to the target sequence have been added, PCR is carried out in the above described manner. The reaction solution may contain, for example, DNA polymerase, dNTP, and various kinds of other additives that can be used in nucleic acid amplification, in addition to the respective primers and the labeled probe.

The timing of adding the labeled probe is not particularly limited. For example, the labeled probe may be added before, during, or after the amplification reaction. Preferably, the labeled probe is added before the amplification reaction because the amplification reaction in the step (a) and the step (b) can be carried out successively.

Next, disassociation of the obtained amplification product (double-stranded DNA) and hybridization of the labeled probe with a single-stranded DNA obtained through the dissociation are carried out. They can be achieved by changing the temperature of the reaction solution, for example.

The heating temperature in the disassociation step is not particularly limited as long as it is a temperature at which the double-stranded amplification product can be disassociated into single strands. For example, the heating temperature is 85° C. to 95° C. The heating time also is not particularly limited, and generally is 1 second to 10 minutes, preferably 1 second to 5 minutes.

The hybridization of the labeled probe with the disassociated single-stranded DNA can be achieved by, for example, lowering the heating temperature in the disassociation step after the completion of the disassociation step. The temperature condition is, for example, 40° C. to 50° C. The time period for conducting a treatment at this temperature is not particularly limited, and is, for example, 1 to 600 seconds.

Then, while changing the temperature of the reaction solution, signal values indicating the melting states of the hybrid of the amplification product and the labeled probe are measured. Specifically, for example, the reaction solution is heated, i.e., the hybrid of the single-stranded DNA and the labeled probe is heated, and the change in signal value accompanying the temperature rise is measured. As described above, in the case where a probe in which cytosine (c) at the end is labeled (guanine quenching probe) is used, fluorescence is reduced (or quenched) in the state where the probe hybridizes with the single-stranded DNA, and fluorescence is emitted in the state where the probe is disassociated. Therefore, the hybrid with reduced (quenched) fluorescence may be heated gradually, and increase in fluorescence intensity accompanying the temperature rise may be measured, for example. When the labeled probe is used, the signal value can be measured under conditions appropriate for a labeling substance of the labeled probe, for example. When there are a plurality of target sites to be detected, and a plurality of kinds of probes are used for polymorphism detection, probes labeled with labeling substances to be detected under different detection conditions may be used, and the respective signal values may be measured under conditions appropriate for the labeling substances of the respective probes, as described above.

When the change in fluorescence intensity is measured, the temperature range used in the measurement is not particularly limited. The initiation temperature is, for example, room temperature to 85° C., preferably 25° C. to 70° C., and the end temperature is, for example, 40° C. to 105° C. The temperature rising rate is not particularly limited, and is, for example, 0.1 to 20° C./sec., preferably 0.3 to 5° C./sec.

Next, change in signal value accompanying the temperature change is analyzed based on the measured signal values, and a temperature at which the largest change (peak) is observed is determined as a Tm value. The change in signal value can be analyzed by, for example, calculating the amount of change in signal value (F) per unit time (t). When the signal value increases accompanying the melting of the hybrid (dissociation into single strands), for example, the amount of increase in signal value (F) per unit time (t) at each temperature or a negative differential value thereof ($-dF/dt$) is calculated from the obtained signal values, and a temperature at which the smallest value is obtained can be determined as the Tm value. Alternatively, a temperature at which the amount of increase in signal value (F) per unit time (t) or a differential value ($dF/dt$) thereof is the largest can be determined as the Tm value. On the other hand, when the signal value decreases accompanying the melting of the hybrid (dissociation into single strands), the Tm value can be determined by calculating the amount of decrease in signal value (F) per unit time (t), contrary to the above procedure, for example.

Instead of raising the temperature of the reaction solution and then measuring the change in signal accompanying the temperature rise as described above, signal values at the time of hybrid formation may be measured and the change in signal value may be analyzed, for example. That is, when a hybrid is formed by lowering the temperature of the reaction system, the change in signal value accompanying the temperature lowering may be measured.

The analysis of the change in signal value can be carried out by, for example, preparing a graph by plotting the relationship between the temperatures and the change in signal value. However, in the analysis step, preparation of the graph is not always necessary.

The Tm value can be calculated using MELTCALC software (www.meltcalc.com), which is known conventionally, or the like, for example. Also, the Tm value can be determined by a nearest neighbor method.

Then, based on the thus-determined Tm value, the kind of the base at the target site, i.e., whether the polymorphism is mutant or normal, for example, is determined. In the Tm analysis, a perfectly complementary hybrid (perfect match) exhibits a higher Tm value indicating dissociation than a hybrid with a single base difference (mismatch). Therefore, the polymorphism at the target site can be determined by determining the Tm value of a hybrid of the probe with a sequence perfectly complementary thereto and the Tm value of a hybrid of the probe with a sequence perfectly complementary thereto excluding one base previously as evaluation standard values. For example, in the case where a probe complementary to a target sequence including a mutant base is used based on an assumption that the target site is mutant, the target site can be determined as mutant when the Tm value of the formed hybrid is the same as the Tm value of the perfectly complementary hybrid. On the other hand, when the Tm value of the formed hybrid is the same as the Tm value of the hybrid with a single base difference (lower than the Tm value of a perfectly complementary hybrid), it can be determined that the target site is normal. Furthermore, when both the Tm values are detected, it can be determined that both a mutant nucleic acid and a normal nucleic acid are present, for example.

In the present invention, instead of raising the temperature of the reaction solution containing the probe, i.e., heating the hybrid, and then measuring the change in signal accompanying the temperature rise as described above, the change in signal at the time of hybrid formation may be measured, for example. That is, when a hybrid is formed by lowering the temperature of the reaction solution containing the probe, the change in signal accompanying the temperature lowering may be measured.

As a specific example, in the case where a labeled probe that shows signals independently and shows no signals when it forms a hybrid (e.g., a guanine quenching probe) is used, the labeled probe emits fluorescence in the state where a single-stranded DNA and the probe are dissociated, and the fluorescence is reduced (or quenched) when the temperature is lowered to allow the labeled probe to form a hybrid. Therefore, the temperature of the reaction solution may be lowered gradually, and decrease in fluorescence intensity accompanying the temperature lowering may be measured, for example. On the other hand, in the case where a labeled probe that shows no signals independently and shows signals when it forms a hybrid is used, the labeled probe does not emit fluorescence in the state where the single-stranded DNA and the probe are dissociated, and the labeled probe emits fluorescence when the temperature is lowered to allow the labeled probe to form a hybrid. Therefore, the temperature of the reaction solution may be lowered gradually, and increase in fluorescence intensity accompanying the temperature lowering may be measured, for example.

In the present invention, the nucleic acid in the sample may be a single-stranded nucleic acid or a double-stranded nucleic acid. When the nucleic acid is a double-stranded nucleic acid, for example, the polymorphism detection method preferably includes, prior to the hybridization in the step (b), the step of dissociating the double-stranded nucleic acid in the sample by heating. By dissociating the double-stranded nucleic acid into single-stranded nucleic acids, hybridization of the detection probe and the target sequence can be carried out efficiently in the subsequent step (b).

<Amplification Reagent>

The amplification reagent according to the present invention is an amplification reagent for use in the method for amplifying a target sequence according to the present invention. The amplification reagent of the present invention is characterized in that: the target sequence includes a target site showing a polymorphism; a base (x) at the target site is either a first base (x1) or a second base (x2); and the amplification reagent contains the primers (X1) and (X2). Preferably, the amplification reagent of the present invention further contains a primer (Y1).

In the amplification reagent of the present invention, the respective primers are the same as described above. The amplification reagent of the present invention further may contain, for example, various components that are to be used in an amplification reaction and described above with regard to the method for amplifying a target sequence according to the present invention. Preferably, the amplification reagent of the present invention is used in a single reaction system.

Furthermore, the amplification reagent of the present invention may be provided as an amplification kit for use in the method for amplifying a target sequence according to the present invention. The respective components may be contained in separate containers, or may be combined as appropriate and contained in the same container. Preferably, the amplification kit includes instructions for use, for example.

<Polymorphism Detection Reagent>

The polymorphism detection reagent according to the present invention is a detection reagent for use in the polymorphism detection method according to the present invention, and is characterized in that it contains: the amplification reagent according to the present invention; and a probe that can hybridize to a sequence including the target site in the template nucleic acid. The polymorphism detection reagent of the present invention preferably is used in a single reaction system.

The polymorphism detection reagent of the present invention further may contain various components that are to be used in an amplification reaction and described above with regard to the polymorphism detection method of the present invention, for example. The polymorphism detection reagent of the present invention may be provided as a polymorphism detection kit of the present invention, for example. Preferably, the polymorphism detection kit includes instructions for use, for example.

Next, examples of the present invention will be described. It is to be noted, however, that the present invention is by no means limited by the following examples.

EXAMPLES

Example 1

In the present example, Tm analysis was conducted with respect to the bcr-abl gene.

Example 1-1

In the present example, using a normal primer having an additional sequence (E1), Tm analysis was conducted with respect to an unpurified blood sample containing the normal bcr-abl gene, and the presence or absence of a false positive was examined.

In the present example, in a partial sequence of the bcr-abl gene shown in SEQ ID NO: 1, the 270th base (y) was set to a detection site. The base y is cytosine (c) or thymine (t). When the base y is cytosine, it can be determined that the detection site is a normal polymorphism (T315), and when the base y is thymine, it can be determined that the detection site is a mutant polymorphism (T315I).

PCR and Tm analysis were conducted using a fully-automated SNP analyzer (I-densy®, ARKRAY, Inc.). First, 10 µl of whole blood collected using an EDTA blood collection tube was mixed with 70 µl of the following diluent 1, thus preparing diluted blood 1. Further, 10 µl of the diluted blood 1 was mixed with 70 µl of the following diluent 2, thus preparing diluted blood 2. 17 µl of the diluted blood 2 was added to a reaction cell designed specifically for the analyzer. The reaction cell was set in the analyzer, and heated at 95° C. for 10 minutes. After the heating, 23 µl of the following first reagent, 13 µl of the following second reagent, and 10 µl of the following third reagent were added to the reaction cell to be mixed with the heat-treated diluted blood 2. This liquid mixture was subjected to PCR and Tm analysis. The PCR was carried out in the following manner. The liquid mixture was first treated at 95° C. for 60 seconds, and then was subjected to 50 cycles of treatment with a treatment at 95° C. for 1 second and at 64° C. for 15 seconds as one cycle. Further, Tm analysis was carried out in the following manner. The mixture was treated at 95° C. for 1 second and 40° C. for 60 seconds. Subsequently, the liquid mixture was heated from 40° C. to 70° C. at a temperature rising rate of 1° C./3 seconds, and during the temperature rise, the change in fluorescence intensity with time was measured. The detection wavelength was set to 520 to 555 nm.

TABLE 1

(Diluent 1, unit: μl)

| | |
|---|---|
| 1 mol/l Tris-HCl (pH 8.0) | 0.7 |
| 10 w/v % SDS | 2.1 |
| 500 mmol/l EDTA (pH 8.0) | 0.014 |
| 10 w/v % NaN₃ | 0.35 |
| Distilled water | 66.836 |
| Total | 70 μl |

(Diluent 2, unit: μl)

| | |
|---|---|
| 1 mol/l Tris-HCl (pH 8.0) | 0.7 |
| 500 mmol/l EDTA (pH 8.0) | 0.014 |
| 10 w/v % NaN₃ | 0.35 |
| Distilled water | 68.936 |
| Total | 70 μl |

TABLE 2

(First reagent, unit: μl)

| | |
|---|---|
| Distilled water | 19.755 |
| 1 mol/l Tris-HCl (pH 8.6) | 0.63 |
| 20 w/v % BSA | 0.5 |
| 10 w/v % NaN₃ | 0.115 |
| 0.94 U/μl Taq polymerase | 2 |
| Total | 23 μl |

(Second reagent, unit: μl)

| | |
|---|---|
| Distilled water | 5.7 |
| 10 w/v % NaN₃ | 0.065 |
| 1 mol/l Tris-HCl (pH 8.6) | 0.35 |
| 2.5 mmol/l dNTP | 4 |
| 80 v/v % Glycerol | 1.56 |
| 1 mol/l MgCl₂ | 0.075 |
| 1 mol/l KCl | 1.25 |
| Total | 13 μl |

(Third reagent, unit: μl)

| | |
|---|---|
| Distilled water | 8.43 |
| 10 w/v % NaN₃ | 0.05 |
| 1 mol/l Tris-HCl (pH 8.6) | 0.27 |
| 100 μmol/l F primer | 0.5 |
| 100 μmol/l $R_{wt}$ primer | 0.125 |
| 100 μmol/l $R_{mt}$ primer | 0.125 |
| 5 μmol/l probe | 0.5 |
| Total | 10 μl |

The F primer is a forward primer. The $R_{wt}$ primer is a reverse primer in which the base at the 3' end is complementary to the normal target site in the sense strand. The $R_{mt}$ primer is a reverse primer in which the base at the 3' end is complementary to the mutant target site in the sense strand.

The sequences of the F primer, the $R_{wt}$ primer, and the $R_{mt}$ primer are shown below. In the sequence of the F primer (Y1) shown below, the underlined portion is an additional sequence noncomplementary to the antisense strand, and the remaining portion is complementary to the antisense strand. Among the $R_{wt}$ primers shown below, the "additional sequence (+) $R_{wt}$ primer" is such that: the underlined portion at the 5' end is the additional sequence (E1) noncomplementary to the sense strand; the remaining portion is the sequence (A1') complementary to the sense strand; the base (G) indicated with a capital letter at the 3' end is a normal base (G) at the target site and to be paired with a normal base (C) at the target site in the sense strand. Among the $R_{wt}$ primers shown below, the "additional sequence (−) $R_{wt}$ primer" is such that: it does not include the additional sequence (E1); it is consists of a sequence (A1') complementary to the sense strand; and the base (G) indicated with a capital letter at the 3' end is a normal base (G) at the target site and is to be paired with a normal base (C) at the target site in the sense strand. The "additional sequence (−) $R_{mt}$ primer" shown below is such that: it does not include the additional sequence (E2); it is consists of a sequence (A2') complementary to the sense strand; and the base (A) indicated with a capital letter at the 3' end is a mutant base (A) at the target site and is to be paired with a mutant base (T) at the target site in the sense strand.

```
F primer
                                       (SEQ ID NO: 2)
5'-ggacggacggaccgtcctcgttgtcttgttggc-3'
BCR-ABL-F1 + ggac R_wt primer
additional sequence (+) R_wt primer
                                       (SEQ ID NO: 3)
5'-ctacgttcccgtaggtcatgaactcaG-3'
T315I-WT-R1 + ctacg additional sequence (−) R_wt primer
                                       (SEQ ID NO: 4)
5'-ttcccgtaggtcatgaactcaG-3'
T315I-WT-R1

R_mt primer
additional sequence (−) R_mt primer
                                       (SEQ ID NO: 5)
5'-aggttcccgtaggtcatgaactcaA-3'
T315I-mt-R2
```

A primer set including the F primer, the additional sequence (+) $R_{wt}$ primer, and the additional sequence (−) $R_{mt}$ primer was used a primer set of Example 1-1. A primer set including the F primer, the additional sequence (−) $R_{wt}$ primer, and the additional sequence (−) $R_{mt}$ primer was used as a primer set of Comparative Example 1-1.

The $Tm_{wt}$ value of a hybrid of the additional sequence (+) $R_{wt}$ primer with the normal target sequence is 60° C.; the $Tm_{wt}$ value of a hybrid of the additional sequence (−) $R_{wt}$ primer with the normal target sequence is 55.4° C.; and the $Tm_{mt}$ value of a hybrid of the additional sequence (−) $R_{mt}$ primer with the mutant target sequence is 59° C.

The sequence of the probe is shown below. The following probe shows a perfect match with a sequence including the mutant target site in the sense strand of the mutant bcr-abl gene. In the following sequence, the base indicated with a capital letter is complementary to the mutant target site. The 5' end of the probe was labeled with a fluorescent dye "BODIPY FL", and the 3' end of the probe was phosphorylated.

5'-(BODIPY FL)-ctcaAtgatgatatagaacg-P-3' (SEQ ID NO: 6)

Figure 5A:
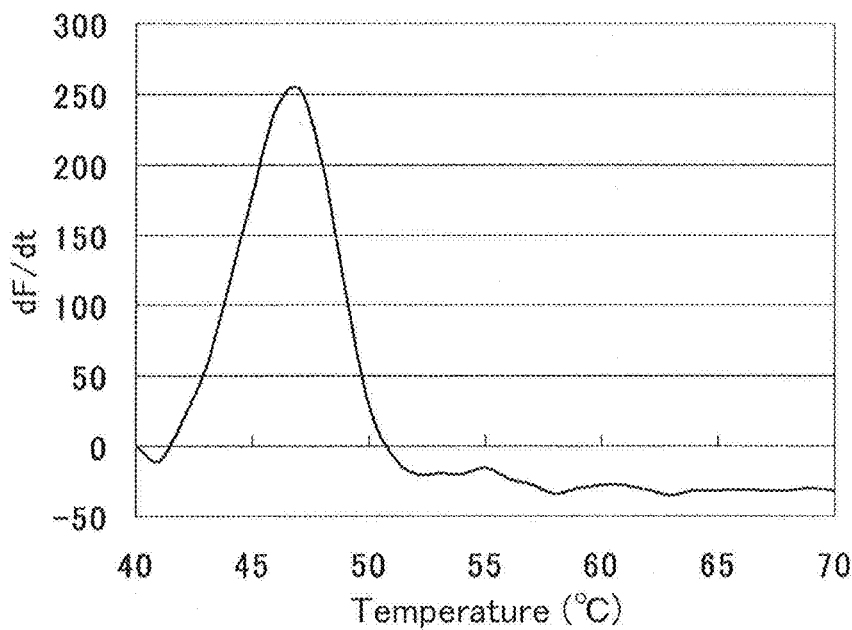
FIG. 5 shows graphs respectively showing the results of Tm analysis in Comparative Example 1-1 and Example 1-1 of the present invention.
Figure 5B:
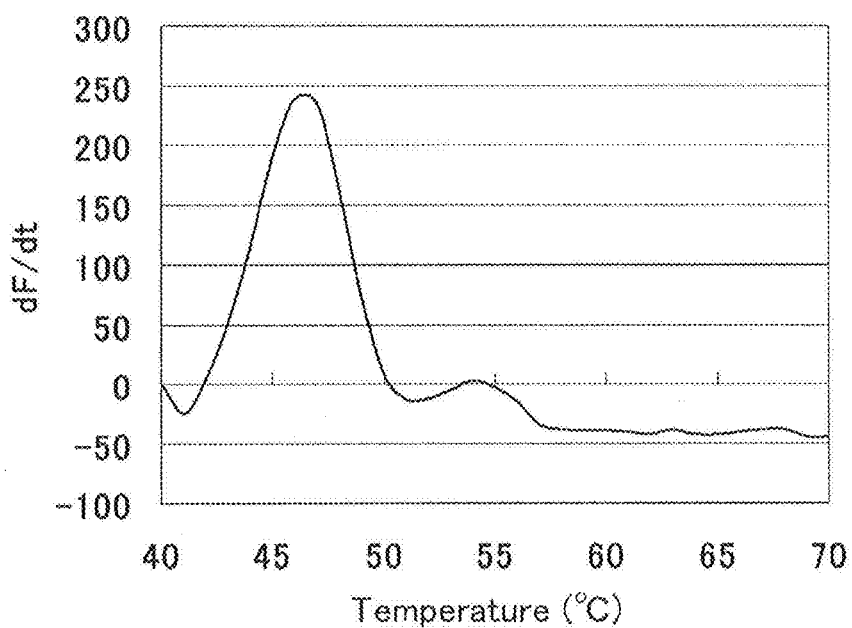

The results are shown in FIG. 5. FIG. 5 show graphs each showing the results of Tm analysis, indicating the change in fluorescence intensity accompanying the temperature rise. FIG. 5A shows the result obtained when the primer set of Example 1-1 was used, and FIG. 5B shows the result obtained when the primer set of Comparative Example 1-1 was used. In FIG. 5, the horizontal axis indicates a temperature (° C.) at the time of the measurement. The vertical axis indicates the change in fluorescence intensity, and the unit thereof is "d amount of change in fluorescence intensity/dt" (dF/dt), which is a differential value of the amount of change in fluorescence intensity. The $Tm_{wt}$ value of a hybrid of the probe with the normal target sequence is 47° C., and the $Tm_{mt}$ value of a hybrid of the probe with the mutant target sequence is 55° C.

Although the polymorphism of the whole blood-derived bcr-abl gene used in the present example was normal as described above, in Comparative Example 1-1 shown in FIG. 5B, a peak was observed not only in the vicinity of the $Tm_{wt}$ value of the hybrid of the probe with the normal target sequence but also in the vicinity of the $Tm_{mt}$ value of the hybrid of the probe with the mutant target sequence. The size of the peak in the vicinity of this $Tm_{mt}$ value is comparable to that of the peak indicating mutation (not shown) observed when 0.3% of mutant genes are present among normal genes. Thus, it was found that this peak indicated a false positive for the mutant polymorphism. In contrast, in Example 1-1 shown in FIG. 5A, a peak was observed only in the vicinity of the $Tm_{wt}$ value of the hybrid of the probe with the normal target sequence, and no peak was observed in the vicinity of the $Tm_{mt}$ value of the hybrid of the probe with the mutant target sequence. The correct result that the mutant polymorphism was not present was obtained with high repeatability (n=4). These results demonstrate that, by using the primers of the present invention, erroneous annealing of a primer and erroneous amplification caused thereby can be prevented, thus inhibiting the occurrence of a false positive, even when an unpurified whole blood sample is used.

Example 1-2

In the present example, using a normal primer having an additional sequence (E1) and a mutant primer having an additional sequence (E2), Tm analysis was conducted with respect to plasmid samples each containing a partial sequence of the bcr-abl gene.

As a partial sequence of the bcr-abl gene, a normal plasmid (WT) and a mutant plasmid (mt) each having an oligonucleotide consisting of 51st to 550th bases in SEQ ID NO: 1 inserted thereto were provided. In the normal plasmid (WT), the 270th base (y) in SEQ ID NO: 1 is cytosine (c), and in the mutant plasmid (mt), the 270th base (y) in SEQ ID NO: 1 is thymine (t). These plasmids were mixed together so as to achieve predetermined ratios shown below, thus preparing two kinds of plasmid samples. The plasmid content in each plasmid sample was $1\times10^4$ copies/W.

|  | Mixed ratio of respective plasmids | |
| --- | --- | --- |
| Plasmid sample | WT | mt |
| mt 1% | 99% | 1% |
| mt 0.3% | 99.7% | 0.3% |

Tm analysis was conducted in the same manner as in Example 1-1, except that a primer set including the F primer and the additional sequence (+) $R_{wt}$ primer of Example 1-1 and an additional sequence (+) $R_{mt}$ primer shown below was used, and 1 μl of the respective plasmid samples and the whole blood sample of Example 1-1 were used. The "additional sequence (+) $R_{mt}$ primer" is such that: the underlined portion at the 5' end is an additional sequence (E2) non-complementary to the sense strand; the remaining portion is the sequence (A2') complementary to the sense strand; and the base (A) indicated with a capital letter at the 3' end is a mutant base (A) at the target site and to be paired with a mutant base (T) at the target site in the sense strand. The additional sequence (E2) of the additional sequence (+) $R_{mt}$ primer was different from the additional sequence (E1) of the additional sequence (+) $R_{wt}$ primer.

The $Tm_{wt}$ value of a hybrid of the additional sequence (+) $R_{wt}$ primer with the normal target sequence is 60° C., and $Tm_{mt}$ value of a hybrid of the additional sequence (+) $R_{mt}$ primer with the mutant target sequence is 63.9° C. The $Tm_{wt}$ value of a hybrid of the sequence (A1'), which is a sequence excluding the additional sequence in the additional sequence (+) $R_{wt}$ primer, with the normal target sequence is 55.4° C., and the $Tm_{mt}$ value of a hybrid of the sequence (A2'), which is a sequence excluding the additional sequence in the additional sequence (+) $R_{mt}$ primer, with the mutant target sequence is 59° C.

```
R_mt primer
additional sequence (+) R_mt primer
                                  (SEQ ID NO: 7)
5'-tgctcaggttcccgtaggtcatgaactcaA-3'
T315I-mt-R2 + tgctc
```

Figure 6A:
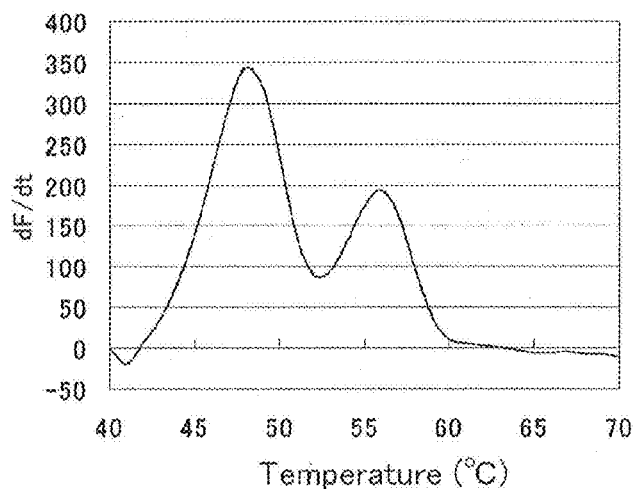
FIG. 6 show graphs each showing the result of Tm analysis in Example 1-2 of the present invention.
Figure 6B:
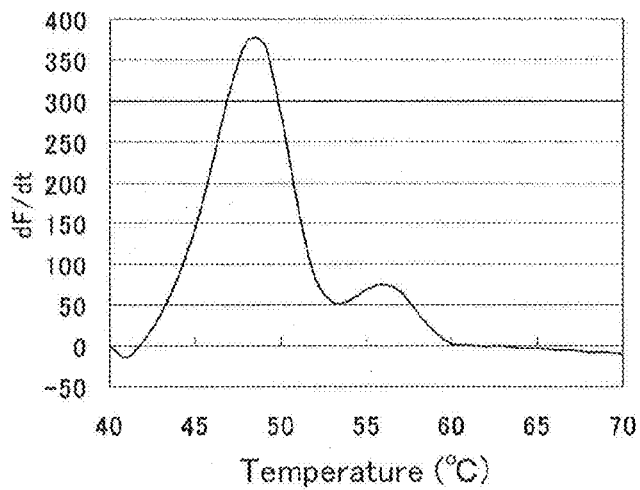
Figure 6C:
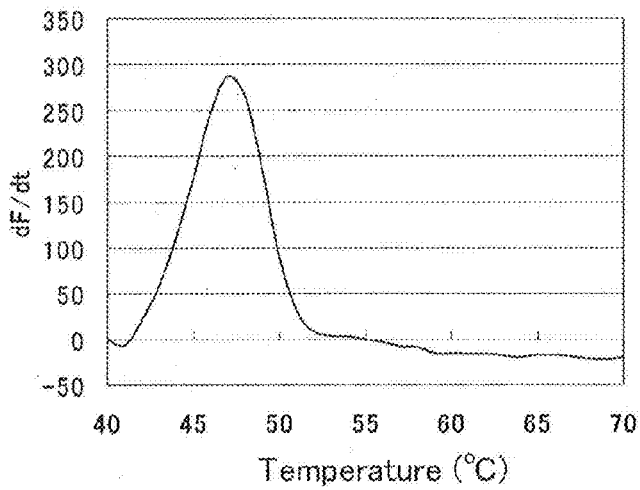

The results are shown in FIG. 6. FIG. 6 show graphs each showing the results of Tm analysis, indicating the change in fluorescence intensity accompanying the temperature rise. FIG. 6A shows the result obtained regarding the plasmid sample mt 1%; FIG. 6B shows the result obtained regarding the plasmid sample mt 0.3%, and FIG. 6C shows the result obtained regarding the whole blood sample. In FIG. 6, the horizontal axis indicates a temperature (° C.) at the time of the measurement. The vertical axis indicates the change in fluorescence intensity, and the unit thereof is "d amount of change in fluorescence intensity/dt" (dF/dt), which is a differential value of the amount of change in fluorescence intensity. The $Tm_{wt}$ value of a hybrid of the probe with the normal target sequence is 47° C., and the $Tm_{mt}$ value of a hybrid of the probe with the mutant target sequence is 55° C.

As can be seen from FIG. 6C, in the case of the normal whole blood sample, a peak was observed only in the vicinity of the $Tm_{wt}$ value of the hybrid with the normal target sequence, and no peak was observed in the vicinity of the $Tm_{mt}$ value of the hybrid with the mutant target sequence. It was found with high repeatability (n=8) that a false positive for the mutant polymorphism could be prevented. Furthermore, as can be seen from FIG. 6A, even when the amount of the mutant plasmid was as small as 1%, a peak could be detected in the vicinity of the $Tm_{mt}$ value of the hybrid with the mutant target sequence. Furthermore, as can be seen from FIG. 6B, even when the amount of the mutant plasmid was as slight as 0.3%, a peak could be detected in the vicinity of the $Tm_{mt}$ value of the hybrid with the mutant target sequence. These results demonstrate that, according to the present invention, a false positive for a mutant polymorphism can be prevented, and also, sufficiently high sensitivity can be realized.

INDUSTRIAL APPLICABILITY

As specifically described above, according to the present invention, it is possible to prevent the above-described erroneous annealing of a primer, for example. As a result, false positive in polymorphism detection is inhibited, thereby allowing the polymorphism detection to be performed with high reliability. Therefore, it can be said that the present invention is very useful in the field of recent clinical practice where treatment and diagnosis are carried out based on the detection of gene polymorphism, for example.

The invention claimed is:

1. A method for detecting a polymorphism in a biological sample as an assay for detecting diseases associated with gene mutations, the method comprising the steps of:
   amplifying a target sequence in a template nucleic acid in a reaction system containing primers (X1) and (X2), and
   detecting a polymorphism at a target site in the target sequence with a probe that hybridizes to the target sequence,
wherein the target sequence comprises the polymorphic target site, and a base (x) at the target site is either a first base (x1) or a second base (x2), wherein:
primer (X1) is
   a primer comprising a sequence (A1') and a sequence (E1),
   the sequence (A1') being complementary to a partial sequence (A1) in the template nucleic acid, and having, in its 3' region, a base (x1') complementary to the first base (x1) at the target site in a 5' region of the partial sequence (A1),
   the sequence (E1) being noncomplementary to a partial sequence (B1) adjacent to a 3' end of the partial sequence (A1) in the template nucleic acid, and being bound to a 5' end of the sequence (A1'), wherein the number of bases in the sequence (E1) is more than 0 but not more than 5; and
primer (X2) is
   a primer comprising a sequence (A2') and a sequence (E2),
   the sequence (A2') being complementary to a partial sequence (A2) in the template nucleic acid, and having, in its 3' region, a base (x2') complementary to the second base (x2) at the target site in a 5' region of the partial sequence (A2),
   the sequence (E2) being noncomplementary to a partial sequence (B2) adjacent to a 3' end of the partial sequence (A2) in the template nucleic acid, and being bound to a 5' end of the sequence (A2'), wherein the sequence (E2) is different from the sequence (E1) and wherein (E2) has the same base length as (E1),
wherein a Tm value of the sequence (A2') of the primer (X2) is higher than a Tm value the sequence (A1') of the primer (X1).

2. The polymorphism detection method according to claim 1, wherein
   in the sequence (A1') of the primer (X1), a base at a 3' end or a second base from the 3' end is the base (x1') complementary to the first base (x1), and
   in the sequence (A2') of the primer (X2), a base at a 3' end or a second base from the 3' end is the base (x2') complementary to the second base (x2).

3. The polymorphism detection method according to claim 1, wherein
   one of the first base (x1) and the second base (x2) is a mutant base ($x_{mt}$) at the target site, and the other is a normal base ($x_{wt}$) at the target site.

4. The polymorphism detection method according to claim 1, further comprising changing a temperature of the reaction system containing an amplification product in the presence of the probe, and measuring a signal value indicating a melting state of a hybrid of the amplification product and the probe; and
   detecting the polymorphism at the target site in the template nucleic acid based on the change in the signal value accompanying the temperature change.

5. A detection reagent for use in the amplification method according to claim 1,
   wherein
      a target sequence in a template nucleic acid comprises a polymorphic target site,
      a base (x) at the target site is either a first base (x1) or a second base (x2), and
      the amplification reagent comprises primers (X1) and (X2), wherein: primer (X1) is
      a primer comprising a sequence (A1') and a sequence (E1),
      the sequence (A1') being complementary to a partial sequence (A1) in the template nucleic acid, and having, in its 3' region, a base (x1') complementary to the first base (x1) at the target site in a 5' region of the partial sequence (A1),
      the sequence (E1) being noncomplementary to a partial sequence (B1) adjacent to a 3' end of the partial sequence (A1) in the template nucleic acid, and being bound to a 5' end of the sequence (A1'), wherein the number of bases in the sequence (E1) is more than 0 but not more than 5; and primer (X2) is
- a primer comprising a sequence (A2') and a sequence (E2),
- the sequence (A2') being complementary to a partial sequence (A2) in the template nucleic acid, and having, in its 3' region, a base (x2') complementary to the second base (x2) at the target site in a 5' region of the partial sequence (A2),
- the sequence (E2) being noncomplementary to a partial sequence (B2) adjacent to a 3' end of the partial sequence (A2) in the template nucleic acid, and being bound to a 5' end of the sequence (A2'), wherein the sequence (E2) is different from the sequence (E1) and wherein (E2) has the same base length as (E1).

6. The detection reagent according to claim 5, wherein
in the sequence (A1') of the primer (X1), a base at a 3' end or a second base from the 3' end is the base (x1') complementary to the first base (x1), and
in the sequence (A2') of the primer (X2), a base at a 3' end or a second base from the 3' end is the base (x2') complementary to the second base (x2).

7. The detection reagent according to claim 5, wherein
one of the first base (x1) and the second base (x2) is a mutant base ($x_{mt}$) at the target site, and the other is a normal base ($x_{wt}$) at the target site.

8. The polymorphism detection method according to claim 1, wherein a difference between a Tm value of the sequence (A2') of the primer (X2) and a Tm value of the sequence (A1') of the primer (X1) is not more than 20° C.

9. The polymorphism detection method according to claim 1, wherein a difference between a Tm value of the sequence (A2') of the primer (X2) and a Tm value of the sequence (A1') of the primer (X1) is not more than 5° C.

10. The polymorphism detection method according to claim 1, wherein the primer (X2) consists of the sequence (A2') and the sequence (E2).

* * * * *